(12) United States Patent
Dener et al.

(10) Patent No.: US 11,827,608 B2
(45) Date of Patent: Nov. 28, 2023

(54) METHOD OF PREPARING PYRIMIDINE CYCLOHEXYL GLUCOCORTICOID RECEPTOR MODULATORS

(71) Applicant: Corcept Therapeutics Incorporated, Menlo Park, CA (US)

(72) Inventors: Jeffrey Mark Dener, Menlo Park, CA (US); Hazel Joan Hunt, West Sussex (GB); Nicholas David Tyrrell, West Sussex (GB)

(73) Assignee: CORCEPT THERAPEUTICS INCORPORATED, Menlo Park, CA (US)

( * ) Notice: Subject to any disclaimer, the term of this patent is extended or adjusted under 35 U.S.C. 154(b) by 29 days.

(21) Appl. No.: 17/556,786

(22) Filed: Dec. 20, 2021

(65) Prior Publication Data

US 2022/0220081 A1 Jul. 14, 2022

Related U.S. Application Data

(60) Provisional application No. 63/128,539, filed on Dec. 21, 2020.

(51) Int. Cl.
| | | |
|---|---|---|
| C07D 239/10 | (2006.01) | |
| C07D 239/36 | (2006.01) | |
| C07D 239/54 | (2006.01) | |

(52) U.S. Cl.
CPC ......... *C07D 239/10* (2013.01); *C07D 239/36* (2013.01); *C07D 239/54* (2013.01)

(58) Field of Classification Search
CPC .............................. C07D 239/36; C07D 239/54
See application file for complete search history.

(56) References Cited

U.S. PATENT DOCUMENTS

| | | |
|---|---|---|
| 6,852,719 B2 | 2/2005 | Liu et al. |
| 7,576,076 B2 | 8/2009 | Clark et al. |
| 7,799,782 B2 | 9/2010 | Munson et al. |
| 8,173,664 B2 | 5/2012 | Clark et al. |
| 8,685,973 B2 | 4/2014 | Clark et al. |
| 8,906,917 B2 | 12/2014 | Clark et al. |
| 9,321,736 B2 | 4/2016 | Clark et al. |
| 9,622,979 B2 | 4/2017 | Bhavarisetti et al. |
| 9,626,979 B2 | 4/2017 | Sung et al. |
| 10,238,659 B2 | 3/2019 | Belanoff et al. |
| 10,881,660 B2 | 1/2021 | Belanoff et al. |
| 11,542,238 B2 | 1/2023 | Hunt et al. |
| 11,548,856 B2 | 1/2023 | Hunt et al. |
| 2005/0245500 A1 | 11/2005 | Roth et al. |
| 2010/0267643 A1 | 10/2010 | Baron et al. |
| 2013/0281324 A1 | 10/2013 | Gouliaev et al. |
| 2021/0238148 A1 | 8/2021 | Hunt et al. |
| 2021/0361651 A1 | 11/2021 | Chia et al. |
| 2021/0363112 A1 | 11/2021 | Hunt et al. |
| 2023/0183186 A1 | 6/2023 | Hunt et al. |

FOREIGN PATENT DOCUMENTS

| | | |
|---|---|---|
| EP | 0037495 A1 | 10/1981 |
| EP | 0369627 A2 | 5/1990 |
| EP | 0722732 A1 | 7/1996 |
| EP | 2313212 A1 | 4/2011 |
| JP | H06128238 A | 5/1994 |
| JP | H1017555 A | 1/1998 |
| JP | 2000271618 A | 10/2000 |
| WO | 0244120 A1 | 6/2002 |
| WO | 03084935 A2 | 10/2003 |
| WO | 2005105036 A1 | 11/2005 |
| WO | 2009014141 A1 | 1/2009 |
| WO | 2010052445 A1 | 5/2010 |
| WO | 2011132094 A2 | 10/2011 |
| WO | 2012129074 A1 | 9/2012 |
| WO | 2016061195 A1 | 4/2016 |
| WO | 2018236749 A2 | 12/2018 |
| WO | 2019236487 A1 | 12/2019 |
| WO | 2021226258 A1 | 11/2021 |
| WO | 2021226260 A1 | 11/2021 |

OTHER PUBLICATIONS

International Search Report and Written Opinion received for PCT Application No. PCTUS2019/035229, dated Oct. 1, 2019, 10 pages.
International Search Report and Written Opinion received for PCT Application No. PCTUS2005/023675, dated Dec. 13, 2005, 11 pages.
International Search Report and Written Opinion received for PCT Application No. PCTUS2012/029376, dated Jun. 27, 2012, 8 pages.
International Search Report and Written Opinion received for PCT Application No. PCT/US2021/030923, dated Aug. 18, 2021, 11 pages.
International Search Report and Written Opinion received for PCT Application No. PCT/US2021/030925, dated Aug. 20, 2021, 12 pages.
Ali et al. (Apr. 2, 2004) "Novel N-Arylpyrazolo[3,2-c]-Based Ligands for the Glucocorticoid Receptor: Receptor Binding and in Vivo Activity", Journal of Medicinal Chemistry, 47(10):2441-2452.
Baptista T. (Jul. 1999) "Body Weight Gain Induced by Antipsychotic Drugs: Mechanisms and Management", Acta Psychiatrica Scandinavica, 100(1):3-16.
Bertagna et al. (Jul. 1984) "The New Steroid Analog RU 486 Inhibits Glucocorticoid Action in Man", The Journal of Clinical Endocrinology and Metabolism, 59(1):25-28.
Bhuyan et al. (1998) "Studies on Uracils: Synthesis of Novel Uracil Analogues via 1,5- and 1,6-Intramolecular Cycloaddition Reactions", Journal of Chemical Research, Synopses, 9:502-503.
Bledsoe et al. (Jul. 12, 2002) "Crystal Structure of the Glucocorticoid Receptor Ligand Binding Domain Reveals a Novel Mode of Receptor Dimerization and Coactivator Recognition", Cell, 110(1):93-105.
Brophy et al. (Jan. 1983) "Bioavailability of Oral Dexamethasone During High Dose Steroid Therapy in Neurological Patients", European Journal of Clinical Pharmacology, 24:103-108.

(Continued)

*Primary Examiner* — Deepak R Rao
(74) *Attorney, Agent, or Firm* — Mintz, Levin, Cohn, Ferris, Glovsky and Popeo, P.C.

(57) ABSTRACT

The present invention provides methods of preparing 2-amino-6-((1r,4r)-4-phenylcyclohexyl)-5-(3-(trifluoromethyl)benzyl)pyrimidin-4(3H)-one, and 2-amino-6-((1r,4r)-4-phenylcyclohexyl)-5-(3-(trifluoromethyl)benzyl)pyrimidin-4(3H)-one monohydrate, as well as new intermediate compounds.

37 Claims, 4 Drawing Sheets

(56) References Cited

OTHER PUBLICATIONS

Cadepond et al. (1997) "RU486 (mifepristone): Mechanisms of Action and Clinical Uses", Annual Review of Medicine, 48:129-156.

Dorwald Florencio Z. (2005) "Side Reactions in Organic Synthesis: A Guide to Successful Synthesis Design", Wiley, VCH, Weinheim p. IX of Preface, 390 pages.

Eyles et al. (Jul. 1997) "Oral Delivery and Fate of Poly(Lactic Acid) Microsphere-Encapsulated Interferon in Rats", Journal of Pharmacy and Pharmacology, 49(7):669-674.

Fotherby K. (Aug. 1996) "Bioavailability of Orally Administered Sex Steroids Used in Oral Contraception and Hormone Replacement Therapy", Contraception, 54(2):59-69.

Fukazawa et al. (1998) "6-Amino-5-Methyluracil Derivativies and Their Use as Thymidine Phosphorylase Inhibitors and Neovascularization Inhibitors", XP002355358; Database CA 'Online'; Chemical Abstracts Service, Columbus, OH, US; Database Accession No. 1998:59356, 4 pages.

Gao et al. (Jun. 1995) "Controlled Release of a Contraceptive Steroid from Biodegradable and Injectable Gel Formulations: In Vitro Evaluation", Pharmaceutical Research, 12(6):857-863.

Groning et al. (May 1996) "Three-dimensional Solubility Parameters and Their Use in Characterising the Permeation of Drugs Through the Skin", Pharmazie, 51(5):337-341.

Hidalgo-Aragones et al. (Aug. 1996) "Pharmacokinetics of oestrone-3-O-sulphamate", The Journal of Steroid Biochemistry and Molecular Biology, 58(5-6):611-617.

Hunt et al. (2012) "Discovery of a Novel Non-steroidal GR Antagonist With in Vivo Efficacy in the Olanzapine-induced Weight Gain Model in the Rat", Bioorganic & Medicinal Chemistry Letters, 22(24):7376-7380.

Johnson et al. (Sep. 1995) "Permeation of Steroids through Human Skin", Journal of Pharmaceutical Sciences, 84(9):1144-1146.

Koorneef et al. (2018) "Selective Glucocorticoid Receptor Modulation Prevents And Reverses Nonalcoholic Fatty Liver Disease In Male Mice", Endocrinology, 159(12):3925-3936.

Lee et al. (Apr. 2020) "Reversal Of Antipsychotic-induced Weight Gain In Rats With Miricorilant, A Selective Glucocorticoid Receptor (Gr) Modulator", American Psychiatric Association Annual Meeting, 1 Page.

Minto et al. (Apr. 1, 1997) "Pharmacokinetics and Pharmacodynamics of Nandrolone Esters in Oil Vehicle: Effects of Ester, Injection Site and Injection Volume", The Journal of Pharmacology and Experimental Therapeutics, 281 (1):93-102.

Nguyen et al. (Sep. 1, 2017) "A Mixed Glucocorticoid/mineralocorticoid Receptor Modulator Dampens Endocrine and Hippocampal Stress Responsivity in Male Rats", Physiology & Behavior, 178:82-92.

Rao K. Paduranga (1995) "Recent Developments of Collagen-Based Materials for Medical Applications and Drug Delivery Systems", Journal of Biomaterials Science, Polymer Edition, 7(7):623-645.

Rohatagi et al. (1995) "Pharmacokinetic and Pharmacodynamic Evaluation of Triamcinolone Acetonide After Intravenous, Oral, and Inhaled Administration", Journal of Clinical Pharmacology, 35(12):1187-1193.

Rohatagi et al. (Sep. 1, 1995) "Pharmacokinetic Interaction Between Endogenous Cortisol and Exogenous Corticosteroids", Die Pharmazie, 50(9):610-613.

Teutsch et al. (Nov. 1, 1991) "Design of Ligands for the Glucocorticoid and Progestin Receptors", Biochemical Society Transactions, 19(4):901-908.

Tjwa et al. (1995) "Budesonide Inhaled Via Turbuhaler: A More Effective Treatment for Asthma than Beclomethasone Dipropionate Via Rotahaler", Annals of Allergy, Asthma & Immunology, 75(2):107-111.

Turner et al. (Oct. 2005) "Structure of the glucocorticoid receptor (NR3C1) gene 5" untranslated region: identification, and tissue distribution of multiple new human exon 1", Journal of Molecular Endocrinology, 5(2):283-292.

Umbricht et al. (Sep. 1994) "Clozapine and Weight Gain", The Journal of Clinical Psychiatry, 55 Suppl B:157-160.

International Search Report and Written Opinion received for PCT Application No. PCT/US2021/064428, dated Apr. 4, 2022, 16 pages.

Deshmukh et al. (1998) "Efficient method for deamination of aminopyrimidines", National Academy Science Letters (India), 21(7-8):247-249.

Shin-Etsu Document (https://www.setylose.com/en/products/healthcare/shinetsu-aqoat) (Jun. 21, 2023).

XRPD of Formula IVa, Form I

DSC of Formula IVa, Form I

METHOD OF PREPARING PYRIMIDINE CYCLOHEXYL GLUCOCORTICOID RECEPTOR MODULATORS

CROSS-REFERENCES TO RELATED APPLICATIONS

This application claims priority to U.S. Provisional Application No. 63/128,539, filed Dec. 21, 2020, which is incorporated herein in its entirety for all purposes.

BACKGROUND

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). In man, glucocorticoid receptors are present in two forms: a ligand-binding GR-alpha of 777 amino acids; and, a GR-beta isoform which lacks the 50 carboxy terminal residues. Since these include the ligand binding domain, GR-beta is unable to bind ligand, is constitutively localized in the nucleus, and is transcriptionally inactive. The GR is also known as the GR-II.

The biologic effects of cortisol, including those caused by hypercortisolemia, can be modulated at the GR level using receptor modulators, such as agonists, partial agonists and antagonists. Several different classes of agents are able to inhibit the physiologic effects of GR-agonist binding. These antagonists include compositions which, by binding to GR, inhibit the ability of an agonist to effectively bind to and/or activate the GR. One such known GR antagonist, mifepristone, has been found to be an effective anti-glucocorticoid agent in humans (Bertagna (1984) J. Clin. Endocrinol. Metab. 59:25). Mifepristone binds to the GR with high affinity, with a dissociation constant (Kd) of 10-9 M (Cadepond (1997) Annu. Rev. Med. 48:129).

In addition to cortisol, the biological effects of other steroids can be modulated at the GR level using receptor modulators, such as agonists, partial agonists and antagonists. When administered to subjects in need thereof, steroids can provide both intended therapeutic effects, e.g., by stimulating glucocorticoid receptor transrepression, as well as negative side effects, e.g. by chronic glucocorticoid receptor transactivation. Miricorilant (CORT-118335) is another such glucocorticoid receptor modulator compound, and has been described previously in PCT Publication No. WO 2012/129074, and U.S. Pat. No. 8,685,973. What is needed in the art are new methods of preparing relacorilant having lower impurity content. Surprisingly, the present invention meets these and other needs. What is needed in the art are new methods for preparing compounds for modulating GR receptors. Surprisingly, the present invention meets these and other needs.

BRIEF SUMMARY OF THE INVENTION

In one embodiment, the present invention provides a method of preparing a compound of Formula I:

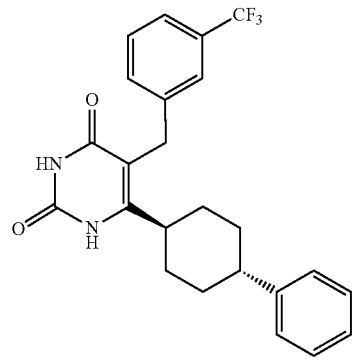

the method comprising: (a) forming a first reaction mixture comprising an oxidizing agent and a compound of Formula II, or a hydrate thereof:

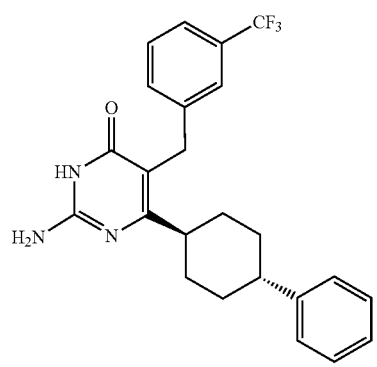

under conditions suitable to prepare the compound of Formula I.

In another embodiment, the present invention provides a method of preparing a compound of Formula I:

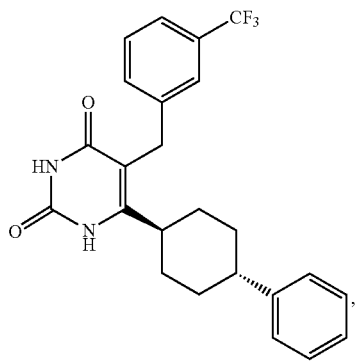

the method comprising:
(e1) forming a seventh reaction mixture comprising dichloromethane, isopropylidene malonate, 1-ethyl-3-(3-dimethylaminopropyl)carbodiimide HCl (EDAC), dimethylaminopyridine (DMAP), and a compound of Formula VI:

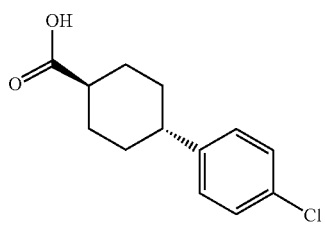

(VI)

under conditions suitable to prepare an intermediate mixture;

(e2) heating a sixth reaction mixture comprising the intermediate mixture and ethanol, thereby preparing a compound of Formula Va:

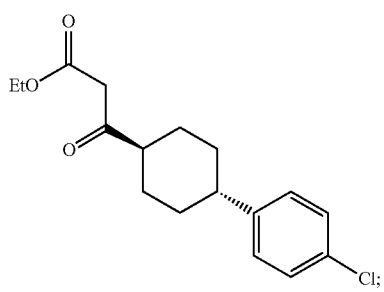

(Va)

(e3) adding heptane to the sixth reaction mixture to crystallize the compound of Formula Va;

(d) forming a fifth reaction mixture comprising ethanol, piperidine, acetic acid, 3-trifluoromethylbenzaldehyde, and the compound of Formula Va, under conditions suitable to prepare a compound of Formula IVa:

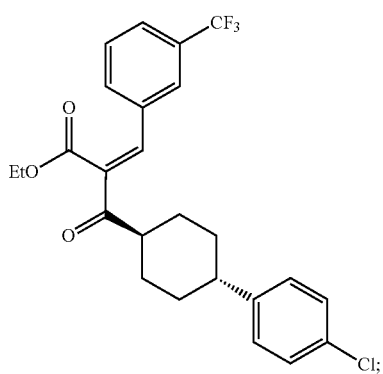

(IVa)

(d1) adding to the fifth reaction mixture a crystalline seed of the compound of Formula IVa to prepare a crystalline form of the compound of Formula IVa;

(c) forming a fourth reaction mixture comprising ethanol, 5% Pd—C, hydrogen, sodium acetate, and the compound of Formula IVa, under conditions suitable to prepare a compound of Formula IIIa:

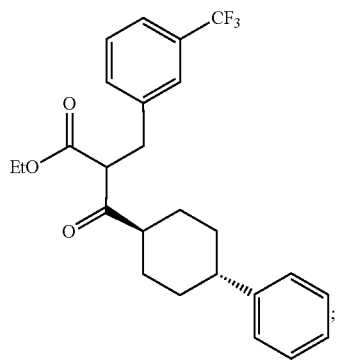

(IIIa)

(b1) forming a third reaction mixture comprising ethanol, guanidine hydrochloride salt and sodium ethoxide to prepare a guanidine free base;

(b) forming a second reaction mixture comprising ethyl acetate, the guanidine free base, and the compound of Formula IIIa, under conditions suitable to prepare a monohydrate form of a compound of Formula II:

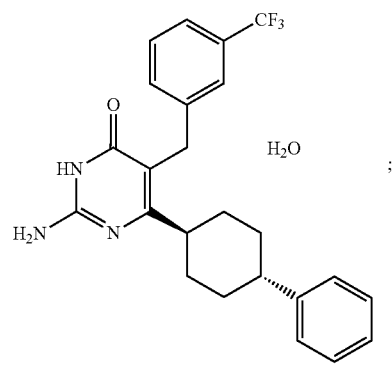 [SMILES: Nc1nc([C@H]2CC[C@H](c3ccccc3)CC2)c(Cc2cccc(C(F)(F)F)c2)c(=O)[nH]1 ; O]

and (a) forming a first reaction mixture comprising acetic acid, sodium nitrite and the monohydrate form of the compound of Formula II, under conditions suitable to prepare the compound of Formula I.

In another embodiment, the present invention provides a method of preparing a compound of Formula II, or a hydrate thereof:

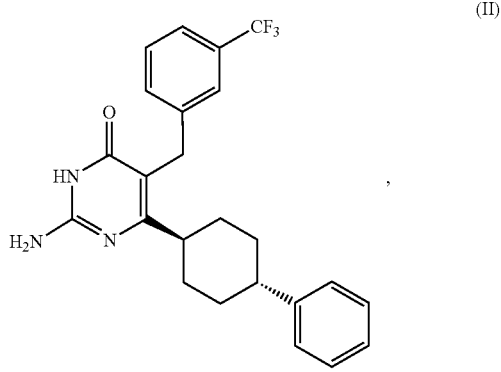 [SMILES: Nc1nc([C@H]2CC[C@H](c3ccccc3)CC2)c(Cc2cccc(C(F)(F)F)c2)c(=O)[nH]1]

(II)

the method comprising: (b) forming a second reaction mixture comprising guanidine and salts thereof, and a compound of Formula III:

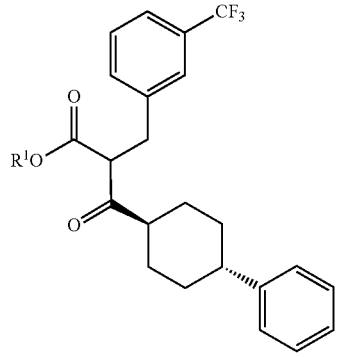
(III)

under conditions suitable to prepare the compound of Formula II, or the hydrate thereof, wherein $R^1$ is $C_{1-6}$ alkyl.

In another embodiment, the present invention provides a compound of Formula II, or a hydrate thereof:

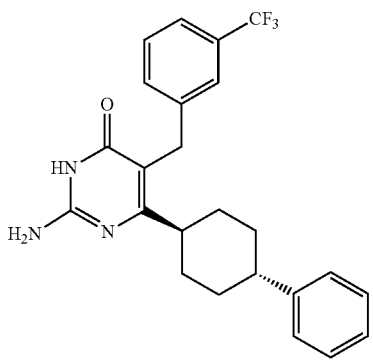
(II)

In another embodiment, the present invention provides a compound of Formula IVa:

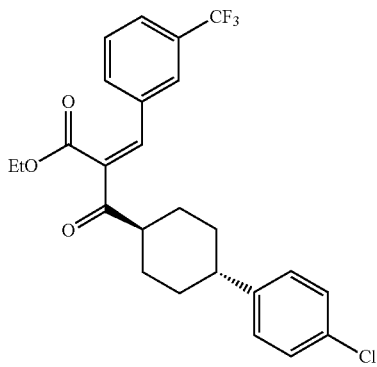
(IVa)

In another embodiment, the present invention provides a compound of Formula Va:

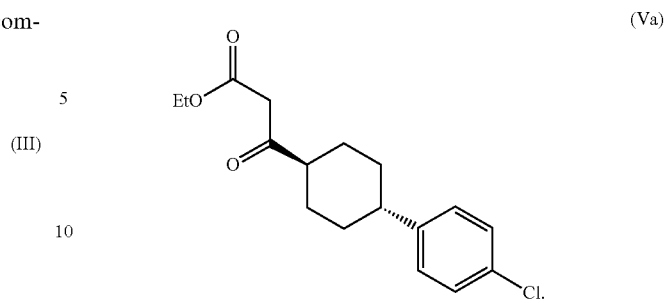
(Va)

DETAILED DESCRIPTION OF THE INVENTION

I. General

Figure 1:
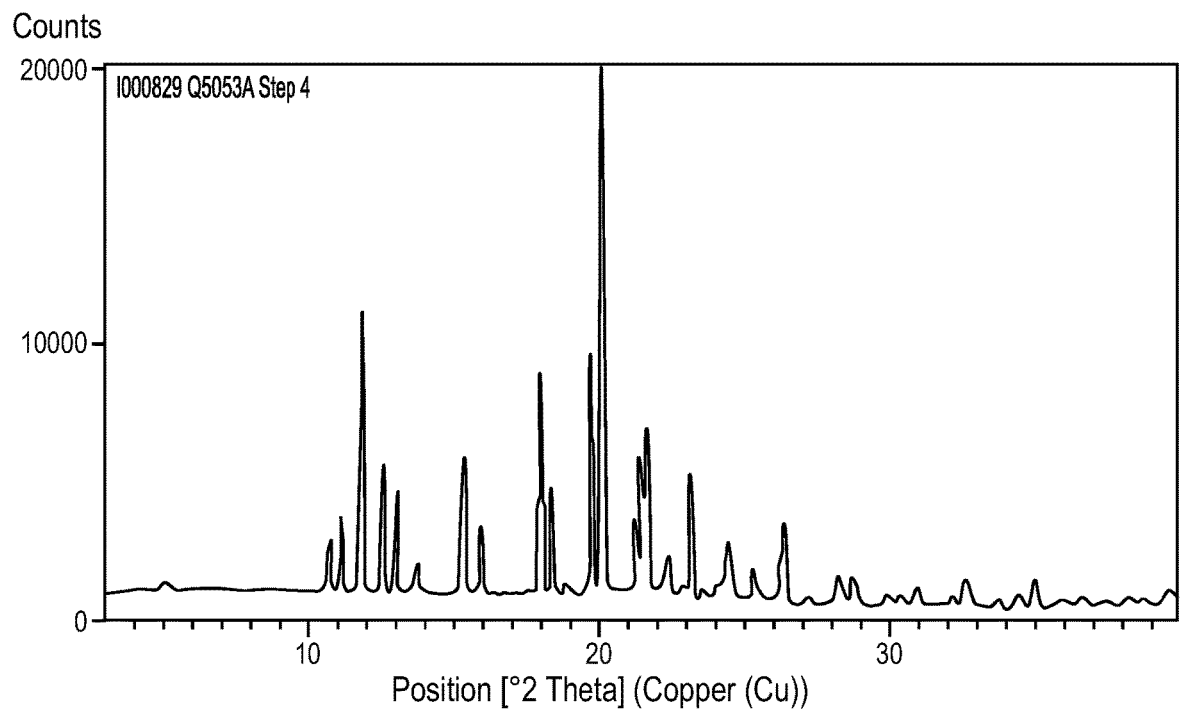
FIG. 1 shows the X-ray pattern diffraction (XRPD) of the compound of Formula II, 2-amino-6-((1r,4r)-4-phenylcyclohexyl)-5-(3-(trifluoromethyl)benzyl)pyrimidin-4(3H)-one.
Figure 2:
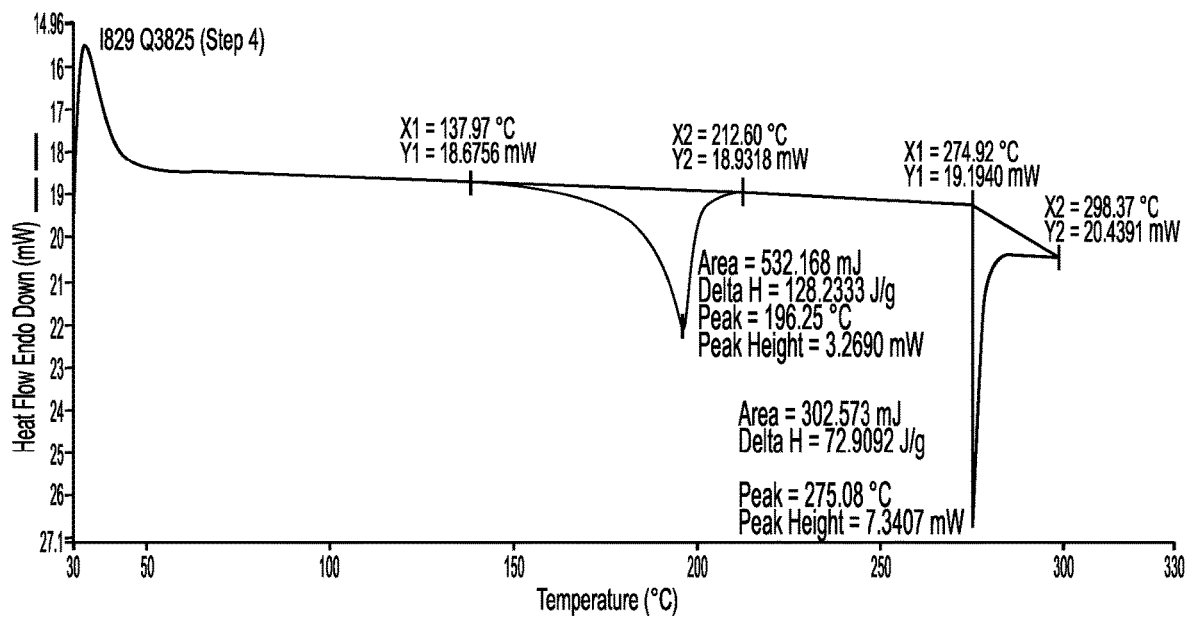
FIG. 2 shows the differential scanning calorimetry of the compound of Formula II.
Figure 3:
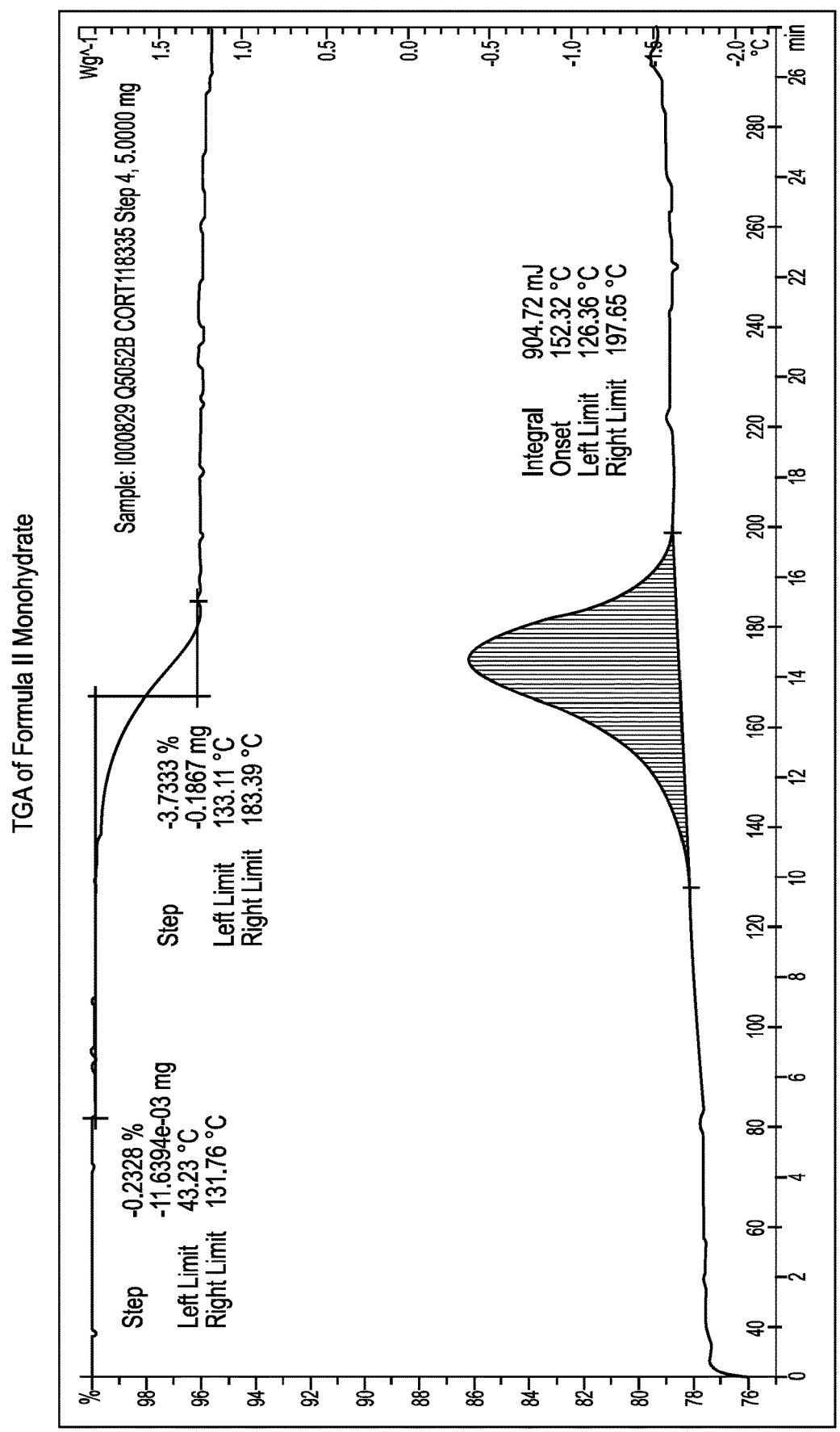
FIG. 3 shows the thermal gravimetric analysis of the compound of Formula II.

The present disclosure describes methods of preparing 6-((1r,4r)-4-phenylcyclohexyl)-5-(3-(trifluoromethyl)benzyl)pyrimidine-2,4(1H,3H)-dione (Formula I), Example 6 of U.S. Pat. No. 8,685,973 via oxidation of the compound of Formula II. The present disclosure also describes methods of preparing 2-amino-6-((1r,4r)-4-phenylcyclohexyl)-5-(3-(trifluoromethyl)benzyl)pyrimidin-4(3H)-one monohydrate (Formula II) by reaction of Formula III, such as Compound 11 of U.S. Pat. No. 8,685,973, with guanidine or salts thereof. The present disclosure also describes new intermediates, including 2-amino-6-((1r,4r)-4-phenylcyclohexyl)-5-(3-(trifluoromethyl)benzyl)pyrimidin-4(3H)-one monohydrate (Formula II), ethyl (Z)-2-((1r,4r)-4-(4-chlorophenyl)cyclohexane-1-carbonyl)-3-(3-(trifluoromethyl)phenyl)acrylate (Formula IVa), and ethyl 3-((1r,4r)-4-(4-chlorophenyl)cyclohexyl)-3-oxopropanoate (Formula Va).

II. Definitions

"About" when referring to a value includes the stated value +/−10% of the stated value. For example, about 50% includes a range of from 45% to 55%, while about 10 equivalents includes a range of w from 9 to 11 equivalents. Accordingly, when referring to a range, "about" refers to each of the stated values +/−10% of the stated value of each end of the range. For instance, a ratio of from about 1 to about 10 (w/w) includes a range of from 0.9 to 11.

"Forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

"Partition mixture" refers to an immiscible mixture of an organic solvent layer and an aqueous water layer used in solvent-solvent extractions in order to isolate a desired substance. Suitable organic solvents include, but are not limited to, hexane, diethyl ether, ethyl acetate, and dichloromethane. Suitable aqueous water layers include, but are not limited to, water, and various water soluble salt solutions, for example, 20% sodium chloride solution.

"Dissolve", "dissolving" or "dissolution" refers to the process of placing a solid material in a solvent system in which the solid material is substantially soluble. For example, the solid material can be greater than 90% soluble in the solvent, or greater than 91, 92, 93, 94, 95, 96, 97, 98, or greater than 99% soluble in the solvent.

"Cooling" refers to applying cooling means to the reaction mixture to decrease the temperature of the reaction mixture by at least 1 degree Celsius. For example, cooling can include, but is not limited to, decreasing the temperature of the reaction mixture below room temperature.

"Heating" refers to applying heat to the reaction mixture to increase the temperature of the reaction mixture by at least 1 degree Celsius. For example, heating can include, but is not limited to, raising the temperature of the reaction mixture to the reflux or boiling temperature of the reaction mixture, or to a temperature between room temperature and the reflux or boiling temperature of the reaction mixture.

"Room temperature" is the range of air temperatures generally considered to be suitable for human occupancy, or between about 15 degrees Celsius (59 degrees Fahrenheit) and 25 degrees Celsius (77 degrees Fahrenheit).

"Acid" refers to a compound capable of donating a proton (a Bronsted-Lowry acid) or capable of accepting an electron pair (a Lewis acid). Representative acids include, but are not limited to, hydrochloric acid, sulfuric acid, formic acid, acetic acid, propanoic acid, butyric acid, hexanoic acid, octanoic acid, trifluoroacetic acid, tetrafluoroboric acid ($HBF_4$), etc.

"Base" refers to a compound capable of accepting a proton (a Bronsted-Lowry base) or capable of donating an electron pair (a Lewis base). Representative bases include, but are not limited to, inorganic bases, organic bases, acid salts, non-nucleophilic bases, and amine bases. For example, the base can be sodium hydroxide, sodium acetate, or mixtures thereof.

"Amine base" or "non-nucleophilic amine base" refers to a nitrogen-containing base that is a moderate to strong base but at the same time is a poor nucleophile. Representative amine bases include bases such as triethylamine, diisopropylethyl amine, N,N-diethylaniline, pyridine, 2,6-lutidine, 2,4,6-collidine, 4-dimethylaminopyridine, and quinuclidine.

"Oxidizing agent" or "oxidizer" refers to a reagent capable of accepting an electron pair from another compound, thus oxidizing the compound. Representative oxidizing agents include, but are not limited to, oxygen, hydrogen peroxide, nitrite, nitric acid, sulfuric acids, etc.

"Reducing agent" refers to a reagent capable of donating an electron to another compound, thus reducing the compound. Representative reducing agents include, but are not limited to, hydrogenation catalysts, hydride reagents such as lithium aluminum hydride ($LiAlH_4$) or sodium borohydride ($NaBH_4$), sodium, formic acid, etc. Hydrogenation catalysts are catalysts that facilitate the hydrogenation of an alkene or other double bond. Representative hydrogenation catalysts include, but are not limited to, Pd/C, Pt, Raney nickel, Ru complexes, Ir complexes, etc.

"Crystalline seed" refers to a seed crystal of the target crystalline form to be prepared.

"Carboxyl coupling agent" refers to a reagent capable of forming an activated ester from a carboxylic acid to facilitate the formation of a carbon-carbon bond at the carbonyl carbon. Representative carboxyl coupling agent include thionyl chloride, carbodiimide reagents, and others.

"Solvent" refers to a substance, such as a liquid, capable of dissolving a solute. Solvents can be polar or non-polar, protic or aprotic. Polar solvents typically have a dielectric constant greater than about 5 or a dipole moment above about 1.0, and non-polar solvents have a dielectric constant below about 5 or a dipole moment below about 1.0. Protic solvents are characterized by having a proton available for removal, such as by having a hydroxy or carboxy group. Aprotic solvents lack such a group. Representative polar protic solvents include alcohols (methanol, ethanol, propanol, isopropanol, etc.), acids (formic acid, acetic acid, etc.) and water. Representative polar aprotic solvents include dichloromethane, chloroform, 1,4-dioxane, tetrahydrofuran, diethyl ether, acetone, ethyl acetate, dimethylformamide, dimethylacetamide, acetonitrile and dimethyl sulfoxide. Representative non-polar solvents include alkanes (pentanes, hexanes, etc.), cycloalkanes (cyclopentane, cyclohexane, etc.), benzene, and toluene. Other solvents are useful in the present invention.

"Water scavenger" refers to a compound or substance that captures water in the reaction mixture to lower the overall water content. Representative water scavengers include alkali aluminosilicates, orthoformates, etc.

"Alkyl" refers to a straight or branched acyclic hydrocarbon containing normal, secondary, or tertiary carbon atoms. For example, an alkyl group can have 1 to 20 carbon atoms (i.e, $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl s-butyl, —$CH(CH_3)CH_2CH_3$), 2-methyl-2-propyl t-butyl, —$C(CH_3)_3$), 1-pentyl (n-pentyl, —$CH_2CH_2CH_2CH_2CH_3$), 2-pentyl s-Pentyl, —$CH(CH_3)CH_2CH_2CH_3$), 3-pentyl (—$CH(CH_2CH_3)_2$), 2-methyl-2-butyl (t-Pn, t-Pentyl, —$C(CH_3)_2CH_2CH_3$), 3-methyl-2-butyl (neo-Pn, neo-Pentyl, —$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Guanidine" refers to the compound having the structure:

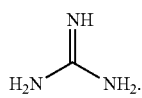

"Isopropylidene malonate" refers to the following structure:

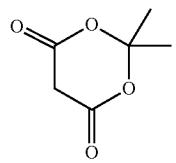

"Tautomer" refers to one of two or more structural isomers which exist in equilibrium and which are readily converted from one isomeric form to another. An example relevant to this application is the two tautomeric forms involving the 2-amino-substituent on the pyrimidine ring of the compound of Formula II, which can exist in either the amino- or imino-forms.

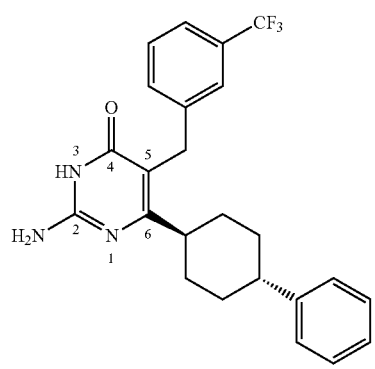

2-Amino tautomer form,
Compound of Formula II

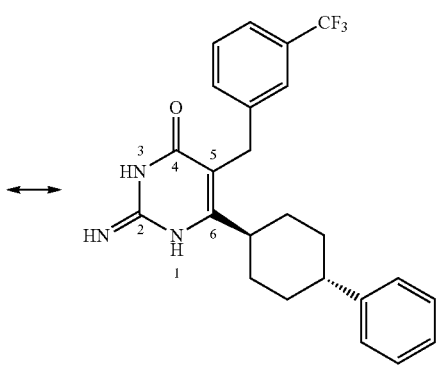

2-Imino tautomer form,
Compound of Formula II

III. Method of Preparing Formula I

The present invention provides methods for the preparation of 6-((1r,4r)-4-phenylcyclohexyl)-5-(3-(trifluoromethyl)benzyl)pyrimidine-2,4(1H,3H)-dione, the compound of Formula I:

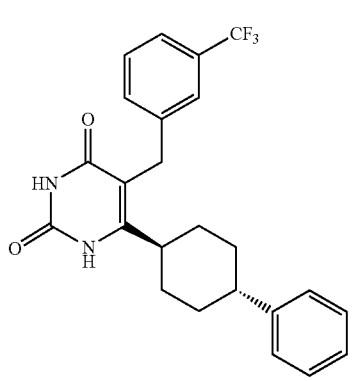

The compound of Formula I was originally disclosed as Example 6 in U.S. Pat. No. 8,685,973.

A. Preparation of Formula I from Formula II

In some embodiments, the present invention provides a method of preparing a compound of Formula I:

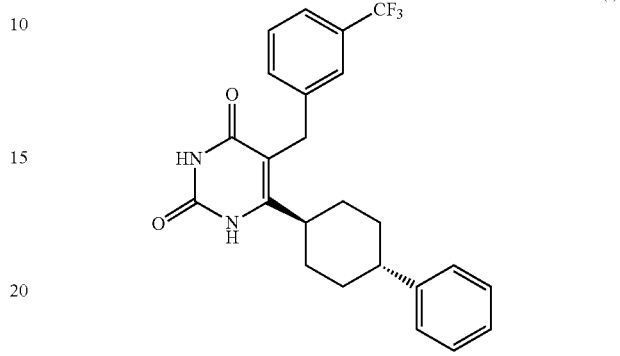

the method comprising: (a) forming a first reaction mixture comprising an oxidizing agent and a compound of Formula II, or a hydrate thereof:

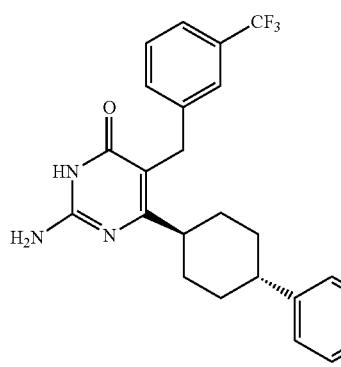

under conditions suitable to prepare the compound of Formula I.

Any suitable oxidizing agent can be used in the method of the present invention. In some embodiments, the oxidizing agent comprises at least one of sodium nitrite (NaNO$_2$), potassium nitrite (KNO$_2$), tetrabutylammonium nitrite [(n-C$_4$H$_9$)$_4$N$^+$NO$_2^-$], nitrosylsulfuric acid, [HOSO$_2$—O—N=O], methyl nitrite (CH$_3$O—N=O), ethyl nitrite (CH$_3$CH$_2$O—N=O), n-propylnitrite (CH$_3$CH$_2$CH$_2$O—N=O), isopropyl nitrite [(CH$_3$)$_2$CHO—N=O], n-butyl nitrite [CH$_3$(CH$_2$)$_3$O—N=O], isobutyl nitrite [(CH$_3$)$_2$CH(CH$_2$)$_2$O—N=O], isopentyl nitrite [(CH$_3$)$_2$CH(CH$_2$)$_2$O—N=O], or phenyl nitrite (C$_6$H$_5$O—N=O). In some embodiments, the oxidizing agent comprises sodium nitrite.

The oxidizing agent can be present in any suitable ratio to the compound of Formula II, or hydrate thereof. For example, the oxidizing agent can be present in a molar ratio of 0.1 to 10 to the compound of Formula II, or 0.1 to 5, 0.5 to 5, 1 to 2, or a molar ratio of 1 to 1.5 to the compound of Formula II. The oxidizing agent can be present in a molar ratio of about 0.5 to the compound of Formula II, or 0.6, 0.7, 0.8, 0.9, 1.0, 1.1, 1.2, 1.3, 1.4, 1.5, 1.6, 1.7, 1.8, 1.9, or a molar ratio of about 2.0 to the compound of Formula II. In some embodiments, the oxidizing agent is present in a molar ratio of about 1.2 to the compound of Formula II.

The first reaction mixture can include a variety of other components. In some embodiments, the first reaction mixture can include a first acid. Representative acids include, but are not limited to, organic acids and inorganic acids. In some embodiments, the first reaction mixture further comprises a first acid comprising hydrochloric acid, sulfuric acid, formic acid, acetic acid, propanoic acid, butyric acid, hexanoic acid, octanoic acid, trifluoroacetic acid, tetrafluoroboric acid (HBF$_4$), or mixtures thereof. In some embodiments, the first acid comprises acetic acid.

The first acid can be present in any suitable amount.

The first reaction mixture can also include a solvent. Representative solvents include non-polar aprotic solvents, polar aprotic solvents, and polar protic solvents. In some embodiments, the first reaction mixture further comprises a first solvent comprising N,N-dimethylformamide (DMF), N,N-dimethylacetamide (DMAc), isopropanol, 2-methyltetrahydrofuran (2-MeTHF), tetrahydrofuran, water, or mixtures thereof.

The compound of Formula II can be the free base form or the hydrate form. In some embodiments, the compound of Formula II can be the free base. In some embodiments, the compound of Formula II can be the hydrate. In some embodiments, the compound of Formula II is the monohydrate form:

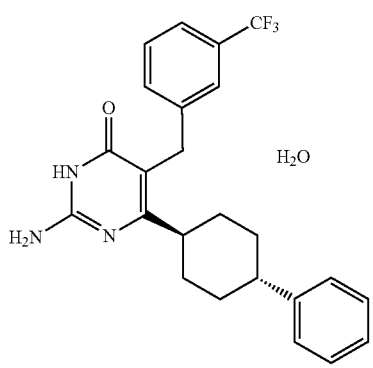

In some embodiments, the first reaction mixture comprises acetic acid, sodium nitrite and the monohydrate form of the compound of Formula II.

The compound of Formula I can be purified by a variety of methods. For example, the compound of Formula I can be crystallized. In some embodiments, the method of preparing the compound of Formula I also includes: (a1) dissolving the compound of Formula I in a solvent mixture comprising methanol in an amount of about 15% (v/v) and dichloromethane in an amount of about 85% (v/v); (a2) heating the solvent mixture to remove dichloromethane and adding methanol to the solvent mixture to replace the removed dichloromethane, thereby preparing a methanol solvent mixture; and (a3) cooling the methanol solvent mixture, thereby forming crystalline Formula I.

The solvent mixture can be heated to any suitable temperature. For example, the solvent mixture can be heated to remove the dichloromethane via distillation at atmospheric pressure.

B. Preparation of Formula II from Formula III

The compound of Formula II, or a hydrate thereof, can be prepared by a variety of methods:

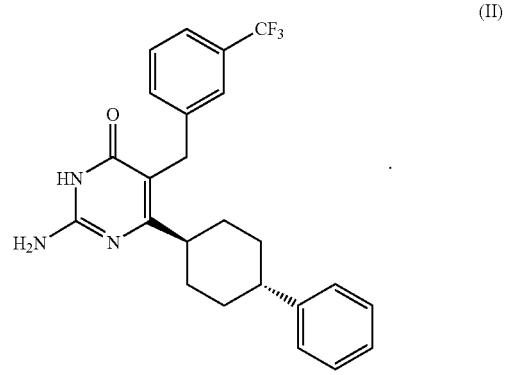 [SMILES: Nc1nc([C@H]2CC[C@H](c3ccccc3)CC2)c(Cc2cccc(C(F)(F)F)c2)c(=O)[nH]1]

In some embodiments, the compound of Formula II, or the hydrate thereof, can be prepared by the method comprising: (b) forming a second reaction mixture comprising guanidine and salts thereof, and a compound of Formula III:

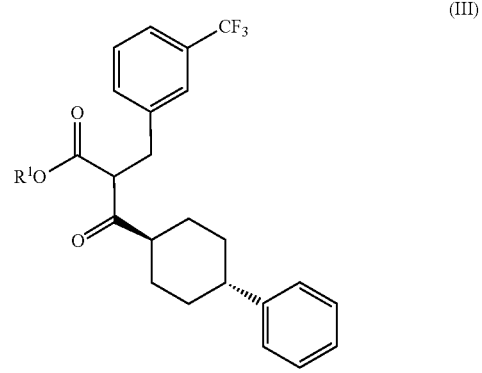

under conditions suitable to prepare the compound of Formula II, or the hydrate thereof, wherein R$^1$ is C$_{1-6}$ alkyl.

Additional embodiments for the preparation of the compound of Formula II are described below in Section IV.

The method of preparing the compound of Formula I can also include the crystallization of the compound of Formula II. In some embodiments, following step (b), the method further comprises: (b2) adding water to the second reaction thereby crystallizing the compound of Formula II, or the hydrate thereof.

In some embodiments, the compound of Formula I is prepared by:
- (b1) forming the third reaction mixture comprising ethanol, guanidine hydrochloride salt and sodium ethoxide to prepare a guanidine free base;
- (b) forming the second reaction mixture comprising ethyl acetate, the guanidine free base, and the compound of Formula IIIa, under conditions suitable to prepare the monohydrate form of the compound of Formula II:

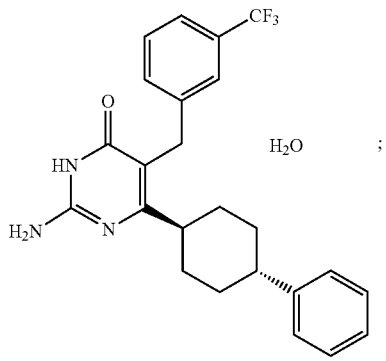 [SMILES: Nc1nc([C@H]2CC[C@H](c3ccccc3)CC2)c(Cc2cccc(C(F)(F)F)c2)c(=O)[nH]1 ; O]

and
- (a) forming the first reaction mixture comprising acetic acid, sodium nitrite and the monohydrate form of the compound of Formula II, under conditions suitable to prepare the compound of Formula I.

C. Preparation of Formula III from Formula IV

The compound of Formula III can be prepared by a variety of methods, such as those described in U.S. Pat. No. 8,685,973:

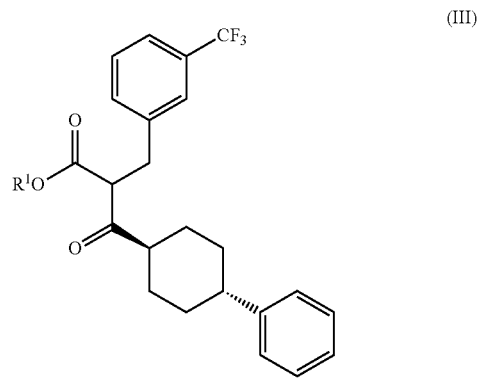

(III)

wherein $R^1$ is $C_{1-6}$ alkyl.

In some embodiments, the compound of Formula III is prepared by: (c) forming a fourth reaction mixture comprising a reducing agent and a compound of Formula IV:

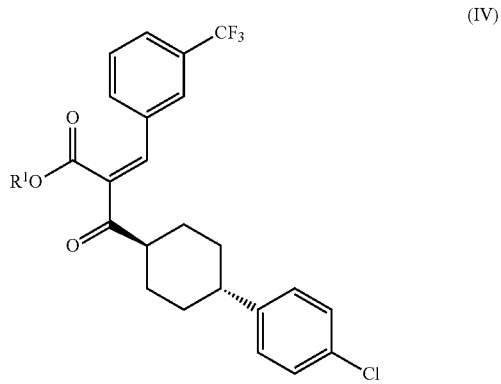

(IV)

under conditions suitable to prepare the compound of Formula III.

The reducing agent can be any suitable reducing agent. In some embodiments, the reducing agent comprises a hydrogenation catalyst, triethylsilane/iron(III) chloride hexahydrate ($Et_3SiH/FeCl_3.6H_2O$), sodium borohydride in pyridine [($NaBH_4$)/pyridine], tri-n-butyltin hydride [($nBu_3SnH$)], tri-(trimethylsilyl)silane [$(Me_3Si)_3SiH$], borane ($BH_3$), and catechol borane [$(o-C_6H_4O_2)BH$], hydrazine ($H_2NNH_2$), formic acid, ammonium formate, cyclohexene, or 1,4-cyclohexadiene. When the reducing agent is the hydrogenation catalyst, the fourth reaction mixture further comprises hydrogen. In some embodiments, the reducing agent is a hydrogenation catalyst and the fourth reaction mixture further comprises hydrogen.

In some embodiments, the reducing agent is the hydrogenation catalyst comprising palladium on carbon (Pd—C), palladium on silicon dioxide, palladium on calcium carbonate, platinum on carbon, palladium hydroxide, platinum hydroxide, palladium(II) chloride, Raney Nickel, rhodium on alumina, rhodium(III) chloride trihydrate/Aliquat 336 (N-methyl N-trioctylammonium chloride), Ru(BINAP)] 2*$NEt_3$, or nickel boride ($Ni_2B$). In some embodiments, the hydrogenation catalyst comprises palladium on carbon (Pd—C).

The reducing agent can be present in any suitable amount. For example, the reducing agent can be present in an equimolar amount to the compound of Formula III, or a catalytic amount. A catalytic amount can be a molar ratio of less than 1 to the compound of Formula III, or a molar ratio less than 0.1 to the compound of Formula III. In some embodiments, the reducing agent is present in a catalytic amount.

The fourth reaction mixture can include a variety of other components, such as a solvent. In some embodiments, the fourth reaction mixture comprises a fourth solvent comprising methanol, ethanol, n-propanol, iso-propanol, n-butanol, ethyl acetate, isopropyl acetate, n-butyl acetate, formic acid, acetic acid, trifluoroacetic acid, water, or mixtures thereof. In some embodiments, the fourth solvent comprises ethanol.

The fourth reaction mixture can also include a base, such as an organic base or an inorganic base. The organic base can be an acid salt, including mono, di or tri salts of a carboxylic acid, sulfuric acid, phosphoric acid, or others. Representative bases include, but are not limited to, potassium acetate, lithium acetate, sodium propionate, sodium butyrate, sodium hexanoate, sodium 2-ethylhexanoate, sodium octanoate, potassium 2-ethylhexanoate, sodium formate, potassium formate, potassium oxalate, sodium oxalate, sodium citrate tribasic, potassium citrate tribasic, nitrilotriacetic acid trisodium salt, ethylenediaminetetraacetic acid (EDTA) disodium salt, or EDTA tetrasodium salt. In some embodiments, the base comprises sodium acetate.

In some embodiments, $R^1$ is $C_{1-6}$ alkyl. In some embodiments, $R^1$ is $C_{1-3}$ alkyl. In some embodiments, $R^1$ is methyl, ethyl, or n-propyl. In some embodiments, $R^1$ is ethyl. In some embodiments the compound of Formula IV is the compound of Formula IVa:

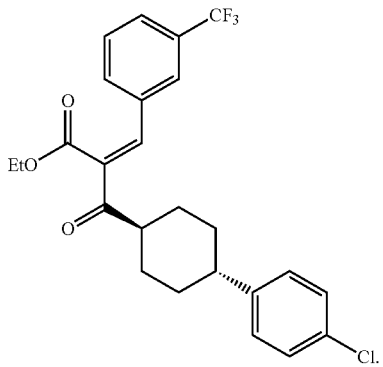

(IVa)

The compound of Formula IVa, has the IUPAC name ethyl (Z)-2-((1r,4r)-4-(4-chlorophenyl)cyclohexane-1-carbonyl)-3-(3-(trifluoromethyl)phenyl)acrylate.

In some embodiments, the fourth reaction mixture comprises ethanol, 5% Pd—C, hydrogen, sodium acetate, and the compound of Formula IV is the compound of Formula IVa:

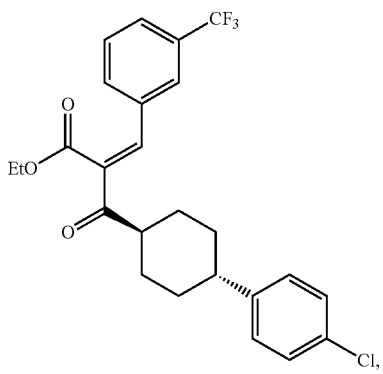

(IVa)

thereby preparing the compound of Formula IIIa:

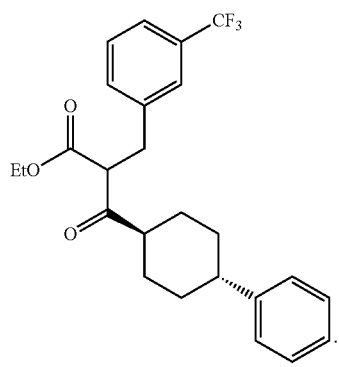

(IIIa)

In some embodiments, the compound of Formula I is prepared by:

(c) forming the fourth reaction comprising ethanol, 5% Pd—C, hydrogen, sodium acetate, and the compound of Formula IVa:

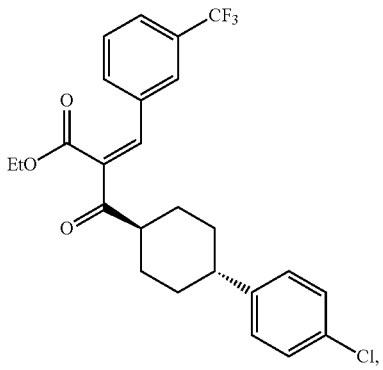

(IVa)

thereby preparing the compound of Formula IIIa:

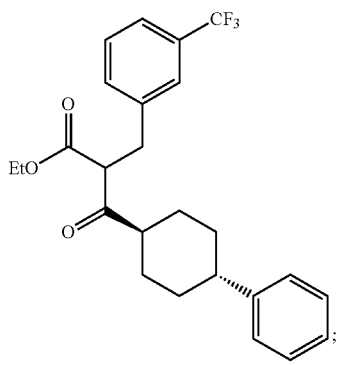

(IIIa)

(b1) forming the third reaction mixture comprising ethanol, guanidine hydrochloride salt and sodium ethoxide to prepare a guanidine free base;

(b) forming the second reaction mixture comprising ethyl acetate, the guanidine free base, and the compound of Formula IIIa, under conditions suitable to prepare the monohydrate form of the compound of Formula II:

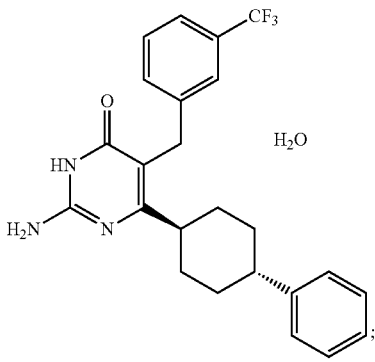 [SMILES: Nc1nc([C@H]2CC[C@H](c3ccccc3)CC2)c(Cc2cccc(C(F)(F)F)c2)c(=O)[nH]1 ; O]

and (a) forming the first reaction mixture comprising acetic acid, sodium nitrite and the monohydrate form of the compound of Formula II, under conditions suitable to prepare the compound of Formula I.

D. Preparation of Formula IV from Formula V

The compound of Formula IV can be prepared by a variety of methods:

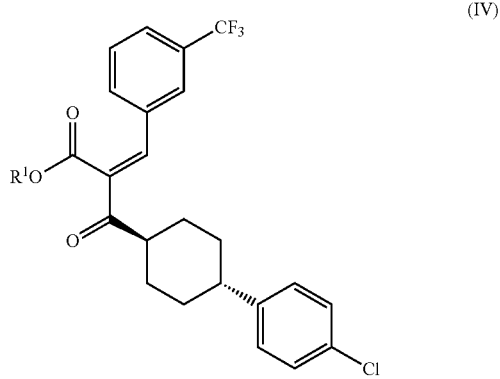

(IV)

wherein R¹ is $C_{1-6}$ alkyl.

In some embodiments, the compound of Formula IV is prepared by: (d) forming a fifth reaction mixture comprising a first amine base, a second acid, 3-trifluoromethylbenzaldehyde, and a compound of Formula V:

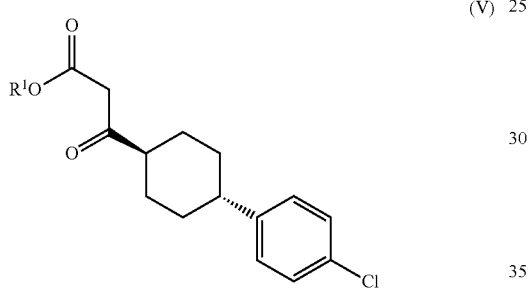

(V)

under conditions suitable to prepare the compound of Formula IV.

The first amine base can be any suitable amine base. In some embodiments, the first amine base comprises triethylamine, N,N-diisopropyl ethylamine (DIPEA), N,N-dimethyl isopropylamine (DIMPA), piperidine, 1-ethylpiperidine, N-methylmorpholine, N-methylpyrrolidine, N,N-dimethylamine, piperazine, N-methylpiperazine, tris(Hydroxymethyl)methylamine [(HOCH₂)₃CNH₂], benzylamine, pyridine, N,N-dimethylaniline, N,N-diethylaniline, 2,6-lutidine, 2,4,6-collidine, 4-dimethyl aminopyridine (DMAP), quinuclidine, 4-pyrrolidinopyridine, 1,4-diazabicyclo[2.2.2]octane (DABCO), or mixtures thereof. In some embodiments, the first amine base comprises piperidine.

The first amine base can be present in any suitable amount. For example, the first amine base can be present in an equimolar amount to the compound of Formula IV, or a catalytic amount. A catalytic amount can be a molar ratio of less than 1 to the compound of Formula IV, or a molar ratio less than 0.1 to the compound of Formula IV. In some embodiments, the first amine base is present in a catalytic amount.

The second acid can be any suitable acid. Representative acids include, but are not limited to, organic acids and inorganic acids. In some embodiments, the second acid can be hydrochloric acid, sulfuric acid, formic acid, acetic acid, propanoic acid, butyric acid, hexanoic acid, octanoic acid, trifluoroacetic acid, tetrafluoroboric acid (HBF₄), or mixtures thereof. In some embodiments, the second acid comprises acetic acid.

The second acid can be present in any suitable amount. For example, the second acid can be present in an equimolar amount to the compound of Formula IV, or a catalytic amount. A catalytic amount can be a molar ratio of less than 1 to the compound of Formula IV, or a molar ratio less than 0.1 to the compound of Formula IV. In some embodiments, the second acid is present in a catalytic amount.

The benzaldehyde can be present in any suitable ratio to the compound of Formula V. For example, the benzaldehyde can be present in a molar ratio of 0.1 to 10 to the compound of Formula V, or 0.1 to 5, 0.5 to 5, 1 to 3, or a molar ratio of 1.5 to 3.5 to the compound of Formula V. The benzaldehyde can be present in a molar ratio of about 1.5 to the compound of Formula V, or 1.6, 1.7, 1.8, 1.9, 2.0, 2.1, 2.2, 2.3, 2.4, or a molar ratio of about 2.5 to the compound of Formula V. In some embodiments, the benzaldehyde is present in a molar ratio of about 2.0 to the compound of Formula V.

In some embodiments, R¹ is $C_{1-6}$ alkyl. In some embodiments, R¹ is $C_{1-3}$ alkyl. In some embodiments, R¹ is methyl, ethyl, or n-propyl. In some embodiments, R¹ is ethyl. In some embodiments, the compound of Formula V is the compound of Formula Va:

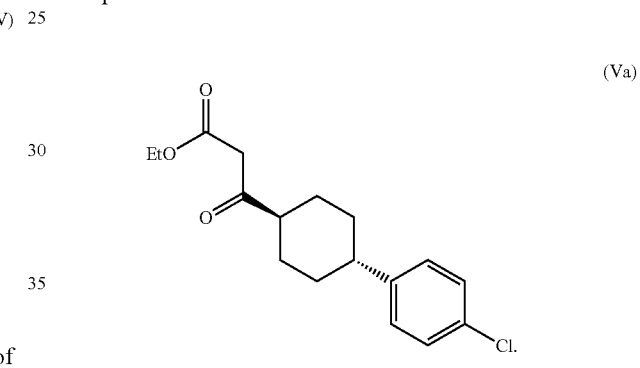

(Va)

The compound of Formula Va has the IUPAC name ethyl 3-((1r,4r)-4-(4-chlorophenyl)cyclohexyl)-3-oxopropanoate.

The fifth reaction mixture can also include a solvent. In some embodiments, the fifth reaction mixture further comprises a fifth solvent comprising methanol, ethanol, n-propanol, iso-propanol, acetonitrile, dichloromethane, diethyl ether, 2-methyltetrahydrofuran (2-MeTHF), cyclopropylmethyl ether (CPME), tetrahydrofuran, 2,2,2-trifluoroethanol, toluene, xylene, mesitylene, or mixtures thereof. In some embodiments, the fifth solvent comprises ethanol.

In some embodiments, the fifth reaction mixture comprises ethanol, piperidine, acetic acid, 3-trifluoromethylbenzaldehyde, and the compound of Formula V is the compound of Formula Va:

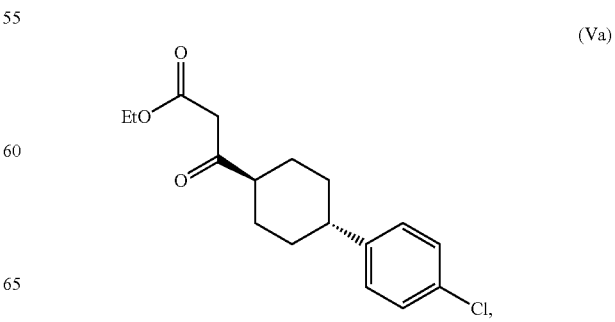

(Va)

thereby preparing the compound of Formula IVa:

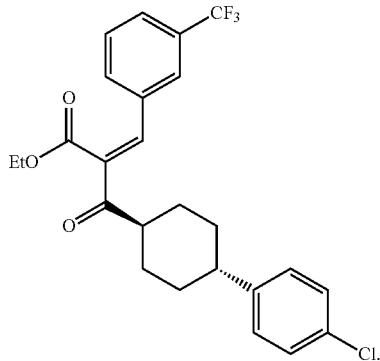

In some embodiments, the compound of Formula I is prepared by:

(d) forming the fifth reaction comprising ethanol, piperidine, acetic acid, 3-trifluoromethylbenzaldehyde, and the compound of Formula Va:

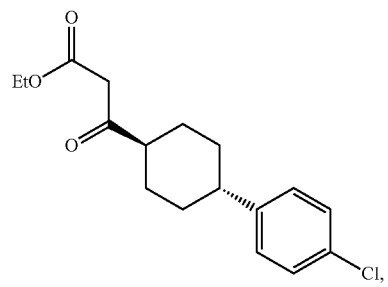

thereby preparing the compound of Formula IVa:

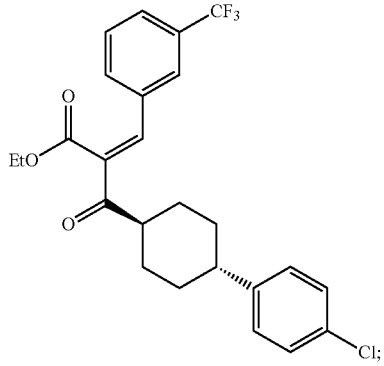

(c) forming the fourth reaction comprising ethanol, 5% Pd—C, hydrogen, sodium acetate, and the compound of Formula IVa, thereby preparing the compound of Formula IIIA:

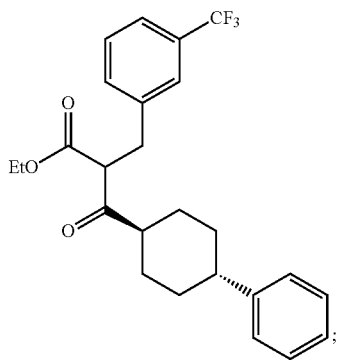

(b1) forming the third reaction mixture comprising ethanol, guanidine hydrochloride salt and sodium ethoxide to prepare a guanidine free base;

(b) forming the second reaction mixture comprising ethyl acetate, the guanidine free base, and the compound of Formula IIIa, under conditions suitable to prepare the monohydrate form of the compound of Formula II:

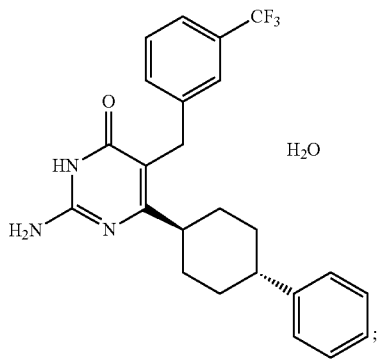

and (a) forming the first reaction mixture comprising acetic acid, sodium nitrite and the monohydrate form of the compound of Formula II, under conditions suitable to prepare the compound of Formula I.

The compound of Formula IV can be crystallized by a variety of methods. In some embodiments, the method of preparing the compound of Formula IV also includes: (d1) adding to the fifth reaction mixture a crystalline seed of the compound of Formula IV to prepare the crystalline form of the compound of Formula IV.

E. Preparation of Formula V from Formula VI

The compound of Formula V can be prepared by a variety of methods

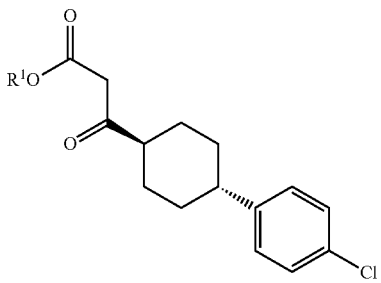

wherein $R^1$ is $C_{1-6}$ alkyl.

In some embodiments, the compound of Formula V is prepared by:

(e1) forming a seventh reaction mixture comprising isopropylidene malonate, a carboxyl coupling agent, a second amine base, and a compound of Formula VI:

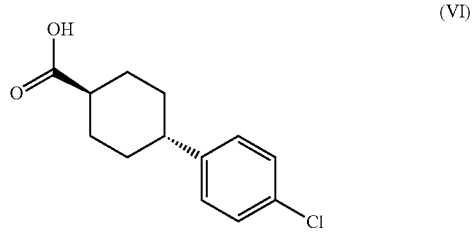 [SMILES: O=C(O)[C@H]1CC[C@H](c2ccc(Cl)cc2)CC1]

(VI)

under conditions suitable to prepare an intermediate mixture; and (e2) heating a sixth reaction mixture comprising the intermediate mixture, thereby preparing the compound of Formula V.

The carboxyl coupling agent can be any agent capable of forming a carbon-carbon bond at the carbonyl carbon of a carboxylic acid. For example, the carboxyl coupling agent can be an agent that forms an activated ester. In some embodiments, the carboxyl activating agent is dicyclohexylcarbodiimide (DCC), N,N'-diisopropylcarbodiimide (DIC), 1-ethyl-3-(3-dimethylaminopropyl)carbodiimide (EDC), 1-ethyl-3-(3-dimethylaminopropyl)carbodiimide HCl (EDAC), bis[[4-(2,2-dimethyl-1,3-dioxolyl)]methyl] carbodiimide (BDDC), N-cyclohexyl-N'-(2-morpholinoethyl)carbodiimide methyl-p-toluenesulfonate, 1-[3-(dimethylamino)propyl]-3-ethylcarbodiimide methiodide, thionyl chloride, oxalyl chloride, 2-ethoxy-1-ethoxycarbonyl-1,2-dihydroquinoline (EEDQ), carbonyl diimidazole, bis(1,2,4-triazolyl)methanone, n-propanephosphonic acid anhydride, ethylmethylphosphonic anhydride (EMPA), cyanuric chloride, 2-chloro-4,6-dimethoxy-1,3,5-triazine (CDMT), 4-(4,6-dimethoxy-1,3,5-triazin-2-yl)-4-methylmorphonium chloride (DMTMM), guanidinium salt, uronium salt, hexafluorophosphate benzotriazole tetramethyl uronium (HBTU), hexafluorophosphate azabenzotriazole tetramethyl uronium (HATU), 2-(1H-benzotriazole-1-yl)-1,1,3,3-tetramethylaminium tetrafluoroborate (TBTU), O-(2-oxo-1(2H)pyridyl)-N,N,N',N'-tetramethyluronium tetrafluoroborate (TPTU), or N-[[[(1-cyano-2-ethoxy-2-oxoethylidene)amino]oxy](dimethylamino)methylene]-N-methyl-methanaminium tetrafluoroborate (TOTU). In some embodiments, the carboxyl activating agent is 1-ethyl-3-(3-dimethylaminopropyl)carbodiimide HCl (EDAC).

The carboxyl activating agent can be present in any suitable ratio to the compound of Formula VI. For example, the carboxyl activating agent can be present in a molar ratio of 0.1 to 10 to the compound of Formula VI, or 0.1 to 5, 0.5 to 5, 1 to 2, or a molar ratio of 1 to 1.5 to the compound of Formula VI. The carboxyl activating agent can be present in a molar ratio of about 0.5 to the compound of Formula VI, or 0.6, 0.7, 0.8, 0.9, 1.0, 1.1, 1.2, 1.3, 1.4, 1.5, 1.6, 1.7, 1.8, 1.9, or a molar ratio of about 2.0 to the compound of Formula VI. In some embodiments, the carboxyl activating agent is present in a molar ratio of about 1.2 to the compound of Formula VI.

The second amine base can be any suitable amine base. In some embodiments, the second amine base comprises triethylamine, N,N-diisopropyl ethylamine (DIPEA), N,N-dimethyl isopropylamine (DIMPA), 1-ethylpiperidine, N-methylmorpholine, N-methylpyrrolidine, pyridine, N,N-dimethylaniline, N,N-diethylaniline, 2,6-lutidine, 2,4,6-collidine, 4-dimethyl aminopyridine (DMAP), quinuclidine, 4-pyrrolidinopyridine, 1,4-diazabicyclo[2.2.2]octane (DABCO), or mixtures thereof. In some embodiments, the second amine base comprises 4-dimethyl aminopyridine (DMAP).

The second amine base can be present in any suitable ratio to the compound of Formula VI. For example, the second amine base can be present in a molar ratio of 0.1 to 10 to the compound of Formula VI, or 0.1 to 5, 0.5 to 5, 1 to 2, or a molar ratio of 1 to 1.5 to the compound of Formula VI. The second amine base can be present in a molar ratio of about 0.5 to the compound of Formula VI, or 0.6, 0.7, 0.8, 0.9, 1.0, 1.1, 1.2, 1.3, 1.4, 1.5, 1.6, 1.7, 1.8, 1.9, or a molar ratio of about 2.0 to the compound of Formula VI. In some embodiments, the second amine base is present in a molar ratio of about 1.1 to the compound of Formula VI.

The isopropylidene malonate can be present in any suitable ratio to the compound of Formula VI. For example, the isopropylidene malonate can be present in a molar ratio of 0.1 to 10 to the compound of Formula VI, or 0.1 to 5, 0.5 to 5, 1 to 2, or a molar ratio of 1 to 1.5 to the compound of Formula VI. The isopropylidene malonate can be present in a molar ratio of about 0.5 to the compound of Formula VI, or 0.6, 0.7, 0.8, 0.9, 1.0, 1.1, 1.2, 1.3, 1.4, 1.5, 1.6, 1.7, 1.8, 1.9, or a molar ratio of about 2.0 to the compound of Formula VI. In some embodiments, the isopropylidene malonate is present in a molar ratio of about 1.1 to the compound of Formula VI.

The seventh reaction mixture can include additional components, such as a solvent. In some embodiments, the seventh reaction mixture further comprises a seventh solvent comprising acetonitrile, tetrahydrofuran, 2-methyltetrahydrofuran, N,N-dimethylformamide, N,N-dimethylacetamide, dichloromethane, chloroform, toluene, or mixtures thereof. In some embodiments, the seventh solvent comprises dichloromethane.

In some embodiments, the seventh reaction mixture comprises dichloromethane, isopropylidene malonate, EDAC, dimethylaminopyridine (DMAP), and the compound of Formula VI.

The sixth reaction mixture can include additional components, such as a solvent. In some embodiments, the sixth reaction mixture further comprises a sixth solvent comprising methanol, ethanol, n-propanol, iso-propanol, n-butanol, t-butanol, pentanol, hexanol, or mixture thereof. In some embodiments, the sixth solvent comprises ethanol.

The compound of Formula V can be crystallized by a variety of methods. In some embodiments, the method of preparing the compound of Formula V also includes the step of: (e3) adding heptane to the sixth reaction mixture to crystallize the compound of Formula V.

In some embodiments, the present invention provides a method of preparing a compound of Formula I:

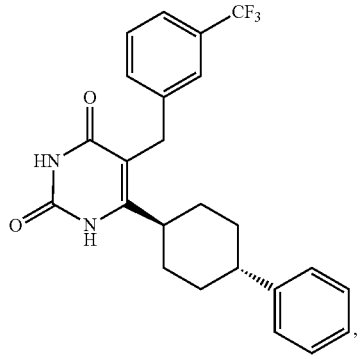

the method comprising:
(e1) forming a seventh reaction mixture comprising dichloromethane, isopropylidene malonate, 1-ethyl-3-(3-dimethylaminopropyl)carbodiimide HCl (EDAC), dimethylaminopyridine (DMAP), and a compound of Formula VI:

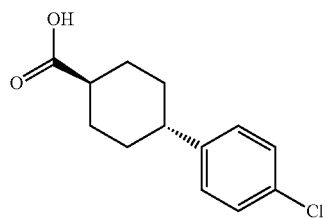

under conditions suitable to prepare an intermediate mixture;
(e2) heating a sixth reaction mixture comprising the intermediate mixture and ethanol, thereby preparing a compound of Formula Va:

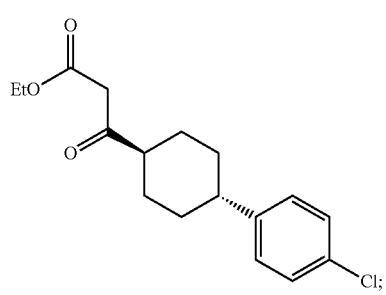

(e3) adding heptane to the sixth reaction mixture to crystallize the compound of Formula Va;
(d) forming a fifth reaction mixture comprising ethanol, piperidine, acetic acid, 3-trifluoromethylbenzaldehyde, and the compound of Formula Va, under conditions suitable to prepare a compound of Formula IVa:

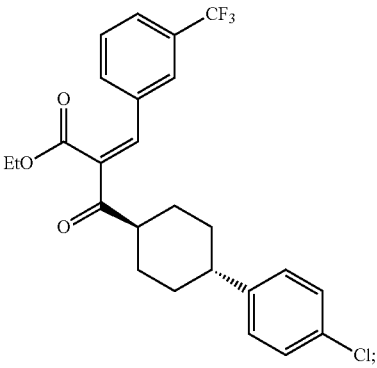

(d1) adding to the fifth reaction mixture a crystalline seed of the compound of Formula IVa to prepare a crystalline form of the compound of Formula IVa;
(c) forming a fourth reaction mixture comprising ethanol, 5% Pd—C, hydrogen, sodium acetate, and the compound of Formula IVa, under conditions suitable to prepare a compound of Formula IIIa:

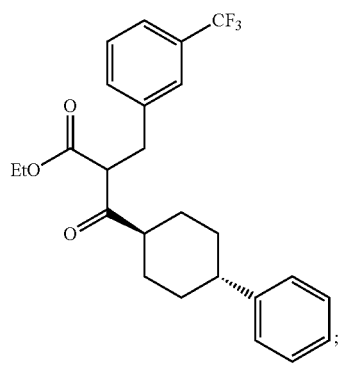

(b1) forming a third reaction mixture comprising ethanol, guanidine hydrochloride salt and sodium ethoxide to prepare a guanidine free base;
(b) forming a second reaction mixture comprising ethyl acetate, the guanidine free base, and the compound of Formula IIIa, under conditions suitable to prepare a monohydrate form of a compound of Formula II:

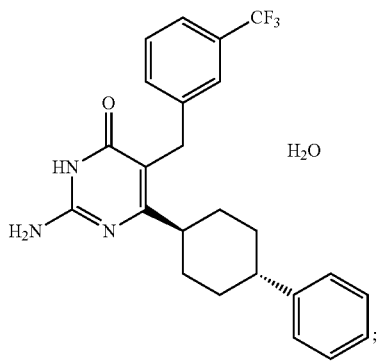

and
(a) forming a first reaction mixture comprising acetic acid, sodium nitrite and the monohydrate form of the compound of Formula II, under conditions suitable to prepare the compound of Formula I.

The method of preparing the compound of Formula I can also include:
(a1) dissolving the compound of Formula I in a solvent mixture comprising methanol in an amount of about 15% (v/v) and dichloromethane in an amount of about 85% (v/v);
(a2) heating the solvent mixture to remove dichloromethane and adding methanol to the solvent mixture to replace the removed dichloromethane, thereby preparing a methanol solvent mixture; and
(a3) cooling the methanol solvent mixture, thereby forming crystalline Formula I.

IV. Method of Preparing Formula II

The present invention also provides methods of preparing 2-amino-6-((1r,4r)-4-phenylcyclohexyl)-5-(3-(trifluoromethyl)benzyl)pyrimidin-4(3H)-one monohydrate. In some embodiments, the present invention provides a method of preparing a compound of Formula II, or a hydrate thereof:

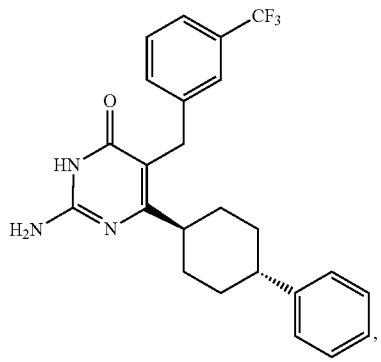

(II)

the method comprising: (b) forming a second reaction mixture comprising guanidine and salts thereof, and a compound of Formula III:

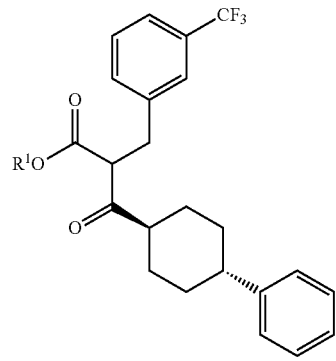

(III)

under conditions suitable to prepare the compound of Formula II, or the hydrate thereof, wherein $R^1$ is $C_{1-6}$ alkyl.

The guanidine can be a free base or a salt form thereof. Representative salt forms of guanidine include, but are not limited to, the hydrochloride salt, the sulfonate salt, the phosphate salt and the acetate salt. In some embodiments, the guanidine is the guanidine free base. In some embodiments, the guanidine is the guanidine salt. In some embodiments, the guanidine is the guanidine hydrochloride salt.

The guanidine can be present in any suitable amount. For example, the guanidine can be present in a molar ratio of 1 to 10 to the compound of Formula III, or 2 to 8, 3 to 7, 4 to 6, or a molar ratio of 4 to 5 to the compound of Formula III. The guanidine can be present in a molar of about 4.0 to the compound of Formula III, or 4.1, 4.2, 4.3, 4.4, 4.5, 4.6, 4.7, 4.8, 4.9, or a molar ratio of about 5.0 to the compound of Formula III. In some embodiments, the guanidine is the guanidine free base present in the molar ratio of about 4.5 to the compound of Formula III. In some embodiments, the guanidine is the guanidine hydrochloride salt present in the molar ratio of about 5.0 to the compound of Formula III.

In some embodiments, $R^1$ is $C_{1-6}$ alkyl. In some embodiments, $R^1$ is $C_{1-3}$ alkyl. In some embodiments, $R^1$ is methyl, ethyl, or n-propyl. In some embodiments, $R^1$ is ethyl. In some embodiments, the compound of Formula III is the compound of Formula IIIa:

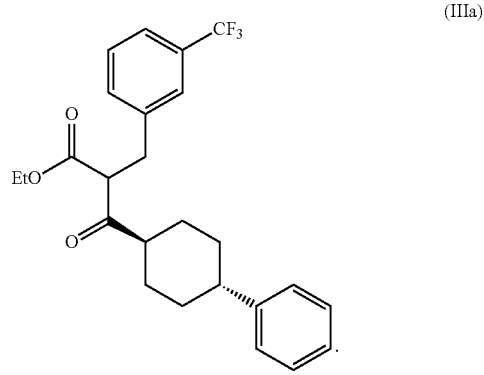 [SMILES: CCOC(=O)C(Cc1cccc(C(F)(F)F)c1)C(=O)[C@H]1CC[C@H](c2ccccc2)CC1]

(IIIa)

The compound of Formula IIIa, having the IUPAC name ethyl 3-oxo-3-((1r,4r)-4-phenylcyclohexyl)-2-(3-(trifluoromethyl)benzyl)propanoate, corresponds to compound 11 of U.S. Pat. No. 8,685,973.

The second reaction mixture can include a variety of additional components, such as a solvent. In some embodiments, the second reaction mixture further comprises a second solvent comprising ethanol, isopropanol, methyl acetate, ethyl acetate, isopropyl acetate, N,N-dimethylformamide (DMF), N,N-dimethylacetamide (DMAc), 2-methyltetrahydrofuran (2-MeTHF), tetrahydrofuran (THF), water, or mixtures thereof. In some embodiments, the second solvent comprises ethyl acetate.

In some embodiments, the second reaction mixture comprises ethyl acetate, guanidine free base, and the compound of Formula IIIa, under conditions suitable to prepare the monohydrate form of the compound of Formula II:

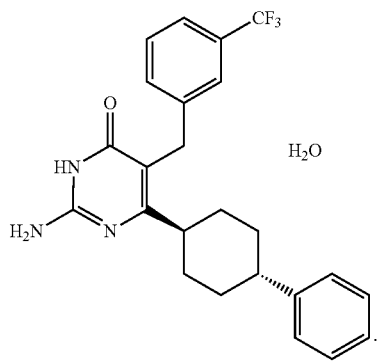 [SMILES: Nc1nc([C@H]2CC[C@H](c3ccccc3)CC2)c(Cc2cccc(C(F)(F)F)c2)c(=O)[nH]1 ; O]

The guanidine free base can be prepared by any suitable methods. In some embodiments, prior to step (b), the method further comprises: (b1) forming a third reaction mixture comprising guanidine salt and a base to prepare the guanidine free base.

In some embodiments, the guanidine salt is the guanidine hydrochloride salt.

Any suitable base can be used in the third reaction mixture. For example, the base can be an organic base or an inorganic base. In some embodiments, the base comprises potassium carbonate, lithium methoxide, potassium methoxide, sodium methoxide, potassium ethoxide, sodium ethoxide, sodium isopropoxide, potassium isopropoxide, potassium tert-butoxide, or sodium tert-butoxide. In some embodiments, the base comprises sodium ethoxide.

The base can be present in any suitable amount. For example, the base can be present in a molar ratio of 1 to 10 to the compound of Formula III, or 2 to 8, 3 to 7, 4 to 6, or a molar ratio of 4 to 5 to the compound of Formula III. The base can be present in a molar of about 4.0 to the compound of Formula III, or 4.1, 4.2, 4.3, 4.4, 4.5, 4.6, 4.7, 4.8, 4.9, or a molar ratio of about 5.0 to the compound of Formula III. In some embodiments, the base is present in the molar ratio of about 4.5 to the compound of Formula III.

The third reaction mixture can include a variety of other components, such as a solvent. In some embodiments, the third reaction mixture further comprises a third solvent comprising methanol, ethanol, n-propanol, iso-propanol, water, or mixtures thereof. In some embodiments, the third solvent comprises ethanol.

In some embodiments, the third reaction mixture further comprises a water scavenger. Representative water scavengers include, but are not limited to, (a) inorganic solids that absorb water: sodium sulfate ($Na_2SO_4$), magnesium sulfate ($MgSO_4$), Crystalline metal aluminosilicates (molecular sieves); (b) organic compounds that chemically react with water: methyl orthoformate [$(MeO)_3CH$], ethyl orthoformate [$(EtO)_3CH$], methyl orthoacetate [$(MeO)_3CMe$], ethyl orthoacetate [$(EtO)_3CMe$], methyl acetate ($MeO_2CMe$), tthyl acetate ($EtO_2CMe$), isopropyl trifluoroacetate (i-$PrO_2CCF_3$); (c) metal alkoxides that react with water: trimethyl borate [$(MeO)_3B$], triethyl borate [$(EtO)_3B$], triisopropyl borate [$(i-PrO)_3B$], tris(2,2,2-trifluoroethyl) borate [$(CF_3CH_2O)_3B$], tetraethyl orthosilicate [$(EtO)_4Si$], tetrakis (2,2,2-trifluoroethoxy)silane [$(CF_3CH_2O)_4Si$], tetrakis(1,1,1,3,3,3-hexafluoro-2-propyloxy)silane [$[(CF_3)_2CHO]4Si$], phenyl Borate [$(PhO)_3B$], triethyl phosphate [$(EtO)_3P$], titanium isopropoxide [$Ti(OPr-i)_4$]; and (d) phosphite esters: trimethyl phosphite [$(MeO)_3P$], triethyl phosphite [$(EtO)_3P$], triisopropyl phosphite [$(i-PrO)_3P$].

In some embodiments, prior to step (b), the method further comprises: (b1) forming the third reaction comprising ethanol, guanidine hydrochloride salt and sodium ethoxide to prepare the guanidine free base.

In some embodiments, the compound of Formula II is prepared by:
(b1) forming the third reaction mixture comprising ethanol, guanidine hydrochloride salt and sodium ethoxide to prepare a guanidine free base;
(b) forming the second reaction mixture comprising ethyl acetate, the guanidine free base, and the compound of Formula IIIa, under conditions suitable to prepare the monohydrate form of the compound of Formula II:

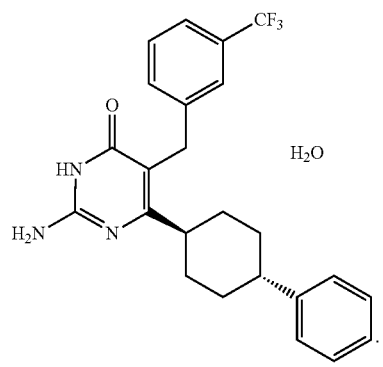 [SMILES: Nc1nc([C@H]2CC[C@H](c3ccccc3)CC2)c(Cc2cccc(C(F)(F)F)c2)c(=O)[nH]1 ; O]

The method of preparing the compound of Formula II can also include the crystallization of the compound of Formula II. In some embodiments, following step (b), the method further comprises: (b2) adding water to the second reaction thereby crystallizing the compound of Formula II, or the hydrate thereof.

V. Compounds

The present invention also provides compounds of Formula II, Formula IVa, and Formula Va, and related crystalline forms.

A. Formula II

In some embodiments, the present invention provides a compound of Formula II, or a hydrate thereof:

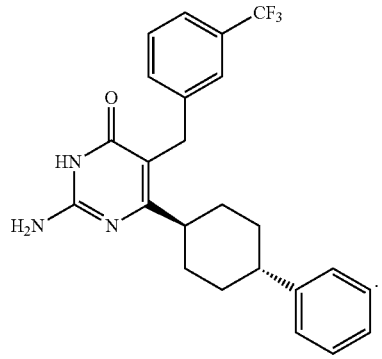 [SMILES: Nc1nc([C@H]2CC[C@H](c3ccccc3)CC2)c(Cc2cccc(C(F)(F)F)c2)c(=O)[nH]1 ; O]

(II)

In some embodiments, the compound of Formula II is the monohydrate form of the compound of Formula II. In some embodiments, the compound of Formula II is the monohydrate having the structure:

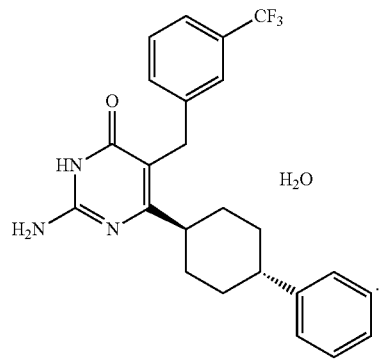

The monohydrate compound of Formula II is named 2-amino-6-(0r,4r)-4-phenylcyclohexyl)-5-(3-(trifluoromethyl)benzyl)pyrimidin-4(3H)-one monohydrate using IUPAC nomenclature.

The compound of Formula II can adopt a variety of physical forms, such as amorphous or crystalline forms. In some embodiments, the monohydrate compound of Formula II is the crystalline form. In some embodiments, the crystalline monohydrate compound of Formula II is characterized by an X-ray diffraction pattern (XRPD) comprising peaks at 20.1, 21.6, 19.7, 11.8, 21.3, 17.9 and 23.1° 2θ±0.2° 2θ. In some embodiments, the crystalline monohydrate compound of Formula II is characterized by an X-ray diffraction pattern (XRPD) further comprising peaks at 10.7, 11.1, 12.6, 13.0, 15.3, 15.9, 18.3, 22.4, 24.4, 25.3, 26.2, 26.3, 28.6, 31.0, 34.5, 35.0° 2θ±0.2° 2θ. In some embodiments, the crystalline monohydrate compound of Formula II is characterized by an X-ray powder diffraction (XRPD) substantially as shown in FIG. 1.

B. Formula IVa

In some embodiments, the present invention provides a compound of Formula IVa:

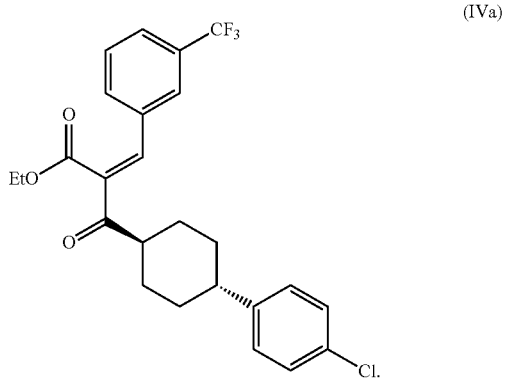 [SMILES: CCOC(=O)/C(=C\c1cccc(C(F)(F)F)c1)C(=O)[C@H]1CC[C@H](c2ccc(Cl)cc2)CC1]

(IVa)

The compound of Formula IVa is named ethyl (Z)-2-(0r,4r)-4-(4-chlorophenyl)cyclohexane-1-carbonyl)-3-(3-(trifluoromethyl)phenyl)acrylate, using IUPAC nomenclature.

Figure 4:
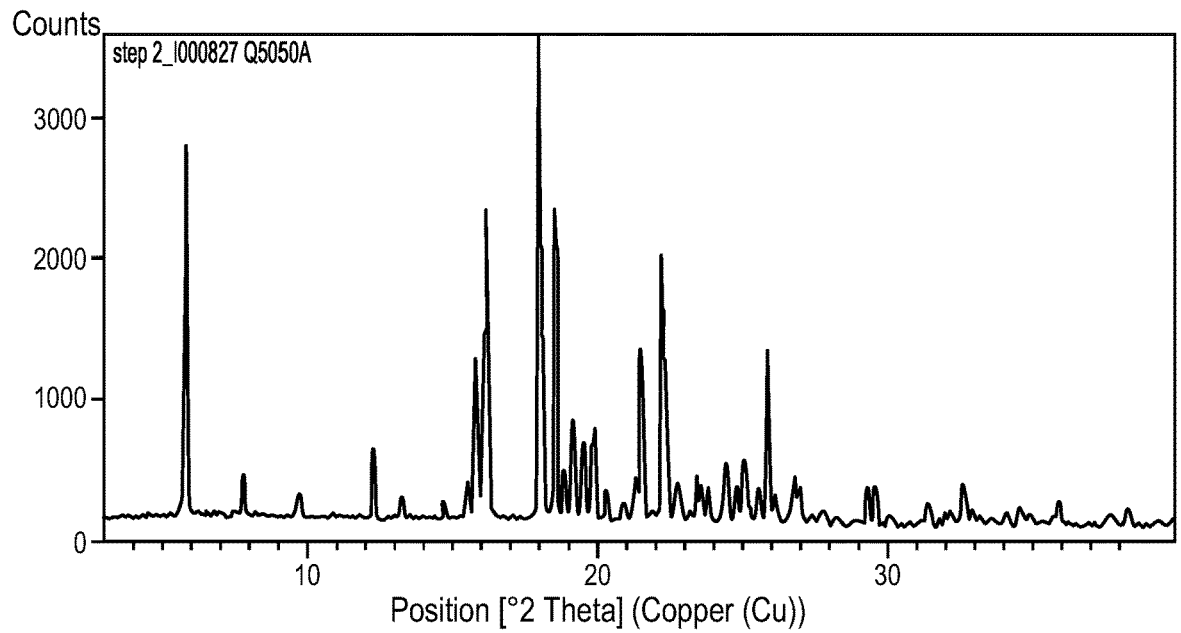
FIG. 4 shows the X-ray pattern diffraction (XRPD) of the compound of Formula IVa, ethyl (Z)-2-((1r,4r)-4-(4-chlorophenyl)cyclohexane-1-carbonyl)-3-(3-(trifluoromethyl)phenyl)acrylate, Form I.
Figure 5:
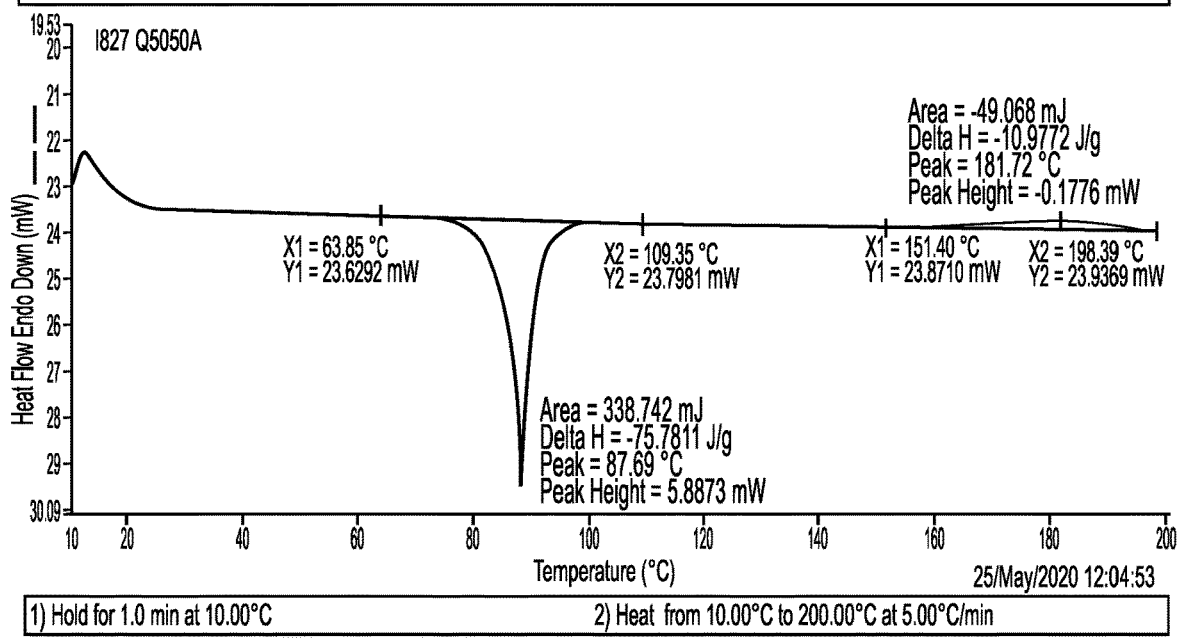
FIG. 5 shows the differential scanning calorimetry of the compound of Formula IVa, Form I.

The compound of Formula IVa can adopt a variety of physical forms, such as amorphous or crystalline forms. In some embodiments, the compound of Formula IVa is a crystalline form. In some embodiments, the crystalline compound of Formula IVa, Form I, is characterized by an X-ray diffraction pattern (XRPD) comprising peaks at 5.9, 16.3, 18.0, 18.6, 22.2 and 25.9° 2 θ±0.2° 2θ. In some embodiments, the crystalline compound of Formula IVa, Form I, is characterized by an X-ray diffraction pattern (XRPD) further comprising peaks at 12.3, 15.8, 16.1, 18.2, 18.9, 19.2, 19.6, 19.9, 21.5, 22.4, 23.5, 24.4, 25.1, 26.8, and 32.6° 2θ±0.2° 2θ. In some embodiments, the crystalline compound of Formula IVa, Form I, is characterized by an X-ray powder diffraction (XRPD) substantially as shown in FIG. 4.

Figure 6:
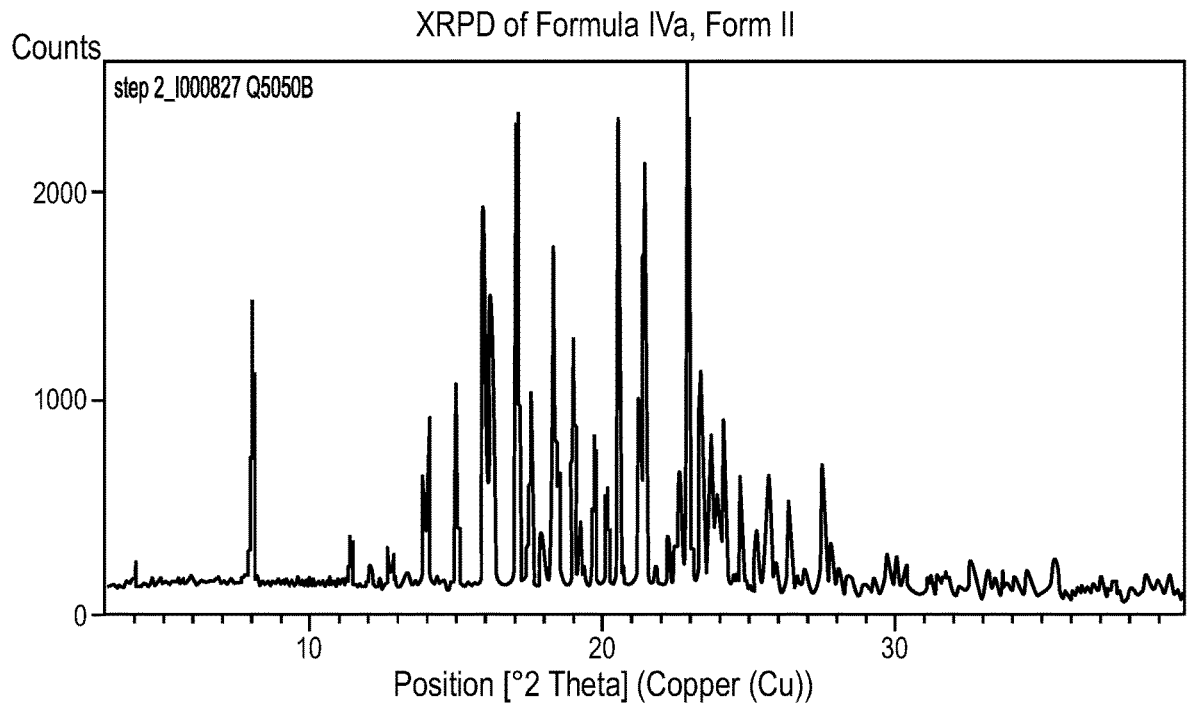
FIG. 6 shows the X-ray pattern diffraction (XRPD) of the compound of Formula IVa, ethyl (Z)-2-((1r,4r)-4-(4-chlorophenyl)cyclohexane-1-carbonyl)-3-(3-(trifluoromethyl)phenyl)acrylate, Form II.
Figure 7:
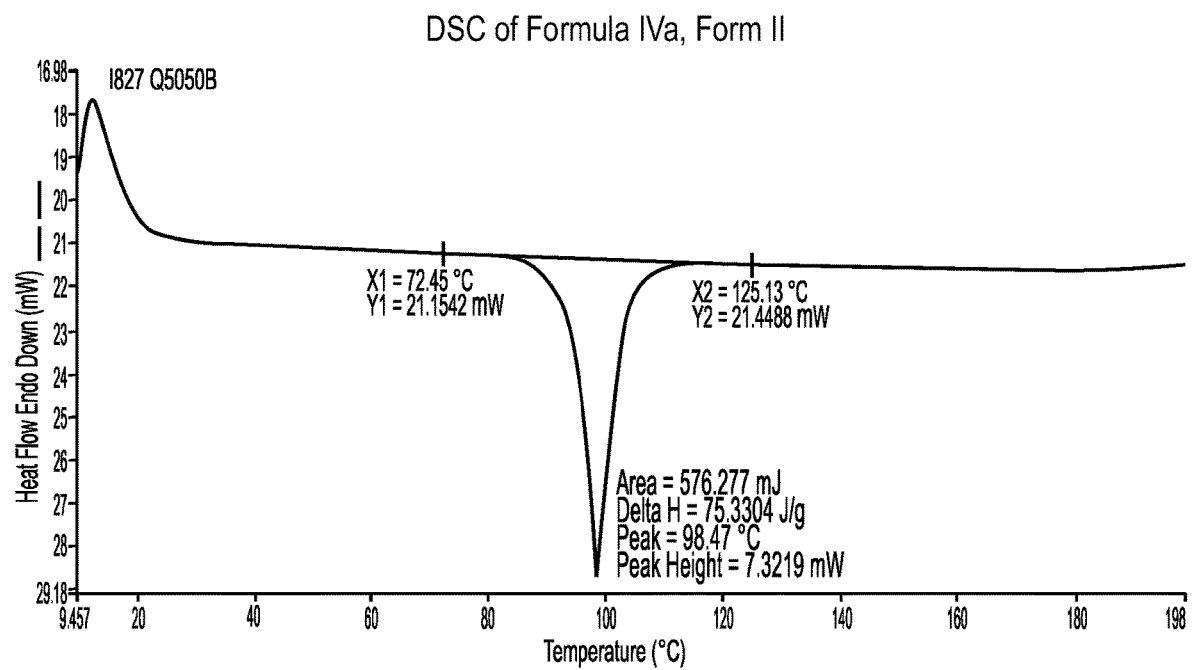
FIG. 7 shows the differential scanning calorimetry of the compound of Formula IVa, Form II.

In some embodiments, the crystalline compound of Formula IVa, Form II, is characterized by an X-ray diffraction pattern (XRPD) comprising peaks at 16.0, 17.1, 18.3, 20.6, 21.4, and 22.9° 2θ±0.2° 2θ. In some embodiments, the crystalline compound of Formula IVa, Form II, is characterized by an X-ray diffraction pattern (XRPD) further comprising peaks at 8.0, 14.1, 15.0, 16.1, 16.2, 17.6, 19.0, 19.7, 21.2, 23.3, 23.4, 23.7, 24.0, 24.1, 24.7, 25.7, 26.4, 27.5, 27.8, 35.5° 2θ±0.2° 2θ. In some embodiments, the crystalline compound of Formula IVa, Form II is characterized by an X-ray powder diffraction (XRPD) substantially as shown in FIG. 6.

C. Formula Va

In some embodiments, the present invention provides a compound of Formula Va:

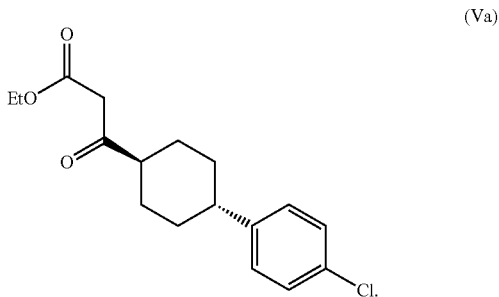 [SMILES: CCOC(=O)CC(=O)[C@H]1CC[C@H](c2ccc(Cl)cc2)CC1]

(Va)

The compound of Formula Va is named ethyl 3-((1r,4r)-4-(4-chlorophenyl)cyclohexyl)-3-oxopropanoate using IUPAC nomenclature.

VI. EXAMPLES

The following abbreviations are used in the methods below:

| | |
|---|---|
| ° C. | Degree Celsius |
| aq | Aqueous |
| atm | Atmospheric pressure |
| DCM | Dichloromethane |
| DMAP | Dimethylaminopyridine |
| EDC | 1-ethyl-3-(3-dimethylaminopropyl)carbodiimide |
| eq | Equivalent |
| g | Gram |
| hdpe | High density polyethylene |
| L | Liter |
| M | Molar |
| mins | Minutes |
| mL | Milliliter |
| Pd—C | Palladium on carbon |
| vol | Volume |
| wrt | With respect to |
| wt | Weight |

X-ray Powder Diffraction (XRPD). XRPD analyses were performed using a Panalytical Xpert Pro diffractometer equipped with a Cu X-ray tube and a Pixcel detector system. The samples were analyzed at ambient temperature in transmission mode and held between PVC films. The Almac default XRPD program was used (range 3-40° 2θ, step size 0.013°, counting time 99 sec, ~22 min run time/counting time 49 sec for the Compound of Formula II and ~11 min run time/counting time 22 sec for the both Forms of the Compound of Formula IVa. Samples were spun at 60 rpm during data collection. XRPD patterns were sorted, manipulated using HighScore Plus 2.2c software.

Differential Scanning calorimetry (DSC). DSC analyses were carried out on a Perkin Elmer Jade Differential Scanning calorimeter. Accurately weighed samples were placed in gold pans and lid secured. Each sample was heated under nitrogen at a rate of 5° C./minute to a maximum of 200 or 300° C.

Thermogravimetric Differential Thermal Analysis (TG-DTA). Thermogravimetric (TG) analyses were carried out on a Mettler Toledo TGA/DSC 1 STAR$^e$ simultaneous thermal analysis instrument. Samples were placed in an aluminium sample pan, inserted into the TG furnace and accurately weighed. Under a stream of nitrogen at a rate of 10° C./minute, the heat flow signal was stabilized for one minute at 30° C., prior to heating to 300° C.

Proton Nuclear Magnetic Resonance Spectroscopy ($^1$H-NMR). Proton NMR analyses were performed on a 500 MHz Bruker AVANCE NEO instrument fitted with a Prodigy BBO CryoProbe. Samples were dissolved in the appropriate deuterated NMR solvent containing tetramethylsilane (TMS) as an internal standard, possessing an isotopic purity of ≥99.5 atom % D, then the solution of the sample was analyzed using 5 mm Virgin NMR tubes.

The reaction steps of the present invention can be performed for any suitable reaction time. For example, the reaction time can be for minutes, hours, or days. In some embodiments, the reaction time can be for several hours, such as at least eight hours. In some embodiments, the reaction time can be for several hours, such as at least overnight. In some embodiments, the reaction time can be for several days. In some embodiments, the reaction time can be for at least two hours. In some embodiments, the reaction time can be for at least eight hours. In some embodiments, the reaction time can be for at least several days. In some embodiments, the reaction time can be for about two hours, or for about 4 hours, or for about 6 hours, or for about 8 hours, or for about 10 hours, or for about 12 hours, or for about 14 hours, or for about 16 hours, or for about 18 hours, or for about 20 hours, or for about 22 hours, or for about 24 hours. In some embodiments, the reaction time can be for about 1 day, or for about two days, or for about three days, or for about four days, or for about five days, or for about six days, or for about a week, or for about more than a week.

The reaction steps of the present invention can be performed at any suitable reaction temperature. Representative temperatures include, but are not limited to, below room temperature, at room temperature, or above room temperature. Other temperatures useful in the methods of the present invention include from about −40° C. to about 65° C., or from about room temperature to about 40° C., or from about 40° C. to about 65° C., or from about 40° C. to about 60° C. In some embodiments, the reaction mixture can be at a temperature of about room temperature, or at a temperature of about 15° C., or at about 20° C., or at about 25° C. or at about 30° C., or at about 35° C., or at about 40° C., or at about 45° C., or at about 50° C., or at about 55° C., or at about 60° C., or at about 65° C.

Example 1. Preparation of Ethyl 3-((1r,4r)-4-(4-chlorophenyl)cyclohexyl)-3-oxopropanoate (Formula Va)

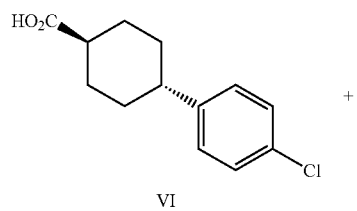

VI
Chemical Formula: C$_{13}$H$_{15}$ClO$_2$
Molecular Weight: 238.71

+

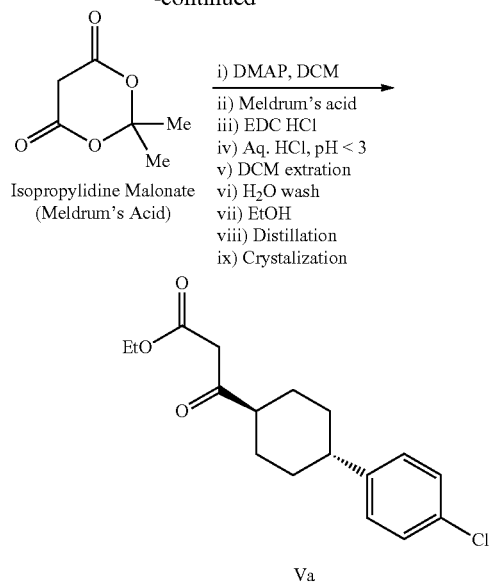

Isopropylidine Malonate (Meldrum's Acid)

i) DMAP, DCM
ii) Meldrum's acid
iii) EDC HCl
iv) Aq. HCl, pH < 3
v) DCM extration
vi) H$_2$O wash
vii) EtOH
viii) Distillation
ix) Crystalization Va
Chemical Formula: C$_{17}$H$_{21}$ClO$_3$
Molecular Weight: 308.80

The compound of Formula Va was prepared by the following procedure.

1. Charge dichloromethane (160 mL, 4.0 vol) to the reactor at 15 to 25° C.
2. Charge trans-4-(4-chlorophenyl)cyclohexanecarboxylic acid (Formula VI; 40.00 g, 1.00 eq) at 15 to 25° C. This forms a mobile slurry.
3. Charge DMAP (22.52 g 1.10 eq) at 15 to 25° C. The slurry thickens substantially.
4. Charge Isopropylidene Malonate (Meldrum's acid) (28.98 g, 1.20 eq) at 15 to 25° C. The slurry largely dissolves.
5. Charge EDC-HCl (38.50 g, 1.20 eq) in 6 equal portions at 15 to 25° C., at approximately 10-15 minute intervals.
6. Adjust temperature, and stir at 20 to 25° C. for 1 to 1.5 hours.
7. Slowly charge 2 M HCl (100 mL, 2.5 vol) to batch at 15-25° C., and agitate for at least 15 minutes. After 15 mins stirring, sample the batch and test the upper aq phase with pH papers, if result is >pH 3, adjust with further 2M HCl.
8. Agitate for at least 15 minutes, allow to settle for at least 15 minutes then separate the phases.
9. Charge dichloromethane (40 mL, 1.0 vol).
10. Agitate for at least 15 minutes, allow to settle for at least 15 minutes then separate the phases.
11. Combine both organic phases in the vessel.
12. Charge water (100 mL, 2.5 vol), agitate for at least 15 minutes, then allow to settle for at least 15 minutes and separate the phases.
13. Return the organic phase, charge water (100 mL, 2.5 vol), agitate for at least 15 minutes, then allow to settle for at least 15 minutes and separate the phases.
14. Return the DCM solution to the vessel.
15. Charge Ethanol (100 mL, 2.5 vol), then heat to boiling at atm pressure (approx. 40° C.).
16. Collect distillate (approx. 243 mL, 6 vol), whilst the batch temperature rises to approximately 65° C. Raise Jacket temp towards 75° C. to achieve this, whilst the batch volume drops to ca 2.5 vols.
17. Charge Ethanol (100 mL, 2.5 vol), and continue the distillation until the batch temperature is above 75° C., expecting ca 0.5- to 1-vol distillate.
18. Hold the batch at reflux (75-78° C.) for 1 to 1.5 hours prior to sampling.
19. Cool the mixture to 40-50° C. and sample.
20. Distil the ethanol solution down to 100 mL (2.5 vol) at approximately 45° C. under vacuum.
21. Adjust the temperature to 40 to 45° C.
22. Charge n-heptane (200 mL, 5 vol) to the ethanol solution keeping the temperature above 30° C.
23. Cool the batch to 15-20° C.
24. Seed the batch with title compound seed [40-50 mg, 0.100 to 0.125 wt % with respect to (wrt) trans-4-(4-chlorophenyl)cyclohexanecarboxylic acid charge], as a slurry in Heptane (0.0100 to 0.0125 vols). Hold at 15-20° C. until the crystallisation has become established. If this does not occur within 2 hours, proceed to next step.
25. Cool batch to 10-15° C., then re-seed with title compound seed (40-50 mg, 0.100 to 0.125 wt %), as a slurry in Heptane (0.0100 to 0.0125 vols) then hold at 10-15° C. until the crystallisation has become established.
26. Once the crystallisation is well established, cool batch to −10±2° C. (−8 to −12° C.) over 2.5-3.5 hours and then hold for at least 8 hours.
27. Filter the slurry, minimizing any delay that leads to warming of the batch.
28. Wash the cake with two portions of n-heptane (60 mL, 1.5 vol) at −5 to 0° C.
29. Pull dry on the filter for at least 1 hour,
30. Dry the material at 40 to 45° C. under vacuum for at least 15 hours.

The characterization data of the title product matched those of Example 6 of U.S. Pat. No. 8,685,973.

Example 2. Preparation of Ethyl (Z)-24(1r,4r)-4-(4-chlorophenyl)cyclohexane-1-carbonyl)-3-(3-(trifluoromethyl)phenyl)acrylate (Formula IVa)

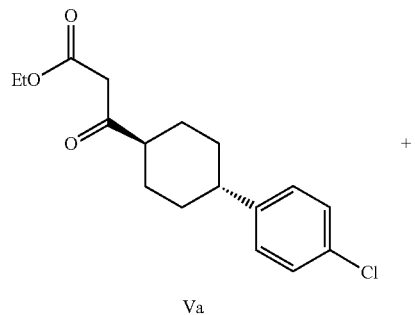

Va
Chemical Formula: $C_{17}H_{21}ClO_3$
Molecular Weight: 308.80

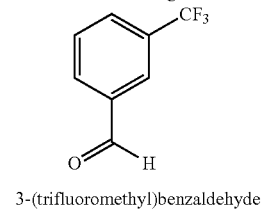

3-(trifluoromethyl)benzaldehyde i) Example I (Va), EtOH
ii) Acetic acid (cat)
iii) Piperidine (cat)
iv) Cool to ~0° C.
v) Filtration
vi) Wash (EtOH)
vii) Dry

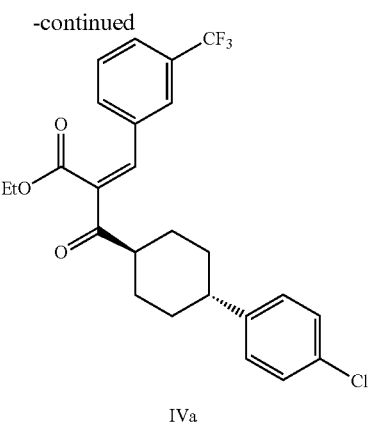

IVa

[(Z)-isomer; Crystalline]
Chemical Formula: $C_{25}H_{24}ClF_3O_3$
Molecular Weight: 464.91

The title compound was prepared according to the following procedure:
1. Charge product of Example 1 (240.0 g, 1 eq) to the reactor.
2. Dispense absolute ethanol (480 mL, 2.0 vol) and charge most of this to the reactor.
3. Commence stirring at 10-25° C., to obtain a slurry.
4. Charge 3-(trifluoromethyl)benzaldehyde (271.0 g, 2.0 eq) at 10 to 25° C. and rinse in with some of the reserved ethanol. The slurry largely dissolves (endothermic).
5. Charge acetic acid (4.67 g, 0.1 eq) at 10 to 25° C. and rinse in with some of the reserved ethanol.
6. Charge piperidine (6.62 g, 0.1 eg) at 10 to 25° C. and rinse in with the last of the reserved ethanol.
7. Adjust the batch to 20±2° C. (18-22° C.), stir for 4-5 hours, then seed the batch with title compound seed (0.24 g, 0.1% wrt product of Example 1), as a slurry in Ethanol (2.4 mL, 0.01 vol).
8. Within two hours of seeding the batch should now be crystallising. If not, repeat the seeding with title compound seed (0.24 g, 0.1% wrt product of Example 1) as a slurry in Ethanol (2.4 mL, 0.01 vol).
9. Once crystallisation is established, continue the reaction for a further 18-24 hours, at 18-22° C., then sample to establish reaction completion.
10. Dilute the batch with absolute ethanol (240 mL, 1 vol).
11. Adjust the reaction mixture to 0±2° C. (−2 to +2° C.) over about 1-2 hours, then hold at 0±2° C. (−2 to +2° C.) for a minimum of 2 hours.
12. Filter the batch, and if necessary return some of the mother liquors to the vessel to complete the transfer.
13. Deliquor the cake thoroughly, and meanwhile chill the absolute ethanol wash (240 mL, 1 vol) in the vessel, to below 10° C.
14. Apply the wash to the cake, and deliquor thoroughly.
15. Repeat the wash with chilled ethanol (240 mL, 1 vol) via the vessel. Deliquor the cake thoroughly
16. Dry the batch under vacuum at 40-50° C.

$^1$H-NMR (500 MHz; CDCl$_3$): δ 7.77 (s, 1H), 7.65 (d, 2H), 7.60 (d, 2H), 7.51 (t, 1H), 7.22 (dt, 2H), 7.06 (dt, 2H), 4.33 (q, 2H), 2.52-2.38 (m, 2H), 1.94 (dd, 4H), 1.52 (qd, 2H), 1.36 (t, 3H), 1.30 (qd, 2H). Melting point (DSC): 98.5° C. (Peak; Form II).

TABLE 1

XRPD Peak Table for Formula IVa, Form I

| Pos. [°2Th.] | Height [cts] | Rel. Int. [%] |
|---|---|---|
| 5.9237 | 2575.99 | 50.25 |
| 7.8835 | 305.01 | 5.95 |
| 9.7399 | 176.11 | 3.44 |
| 12.3314 | 496.13 | 14.52 |
| 13.2976 | 137.63 | 4.03 |
| 14.7625 | 126.27 | 2.46 |
| 15.565 | 268.03 | 9.15 |
| 15.8286 | 1149.29 | 33.63 |
| 16.1283 | 1308.45 | 25.52 |
| 16.2676 | 2152.51 | 62.98 |
| 17.7244 | 105.78 | 4.13 |
| 18.0376 | 3417.67 | 100 |
| 18.1794 | 1191.91 | 29.06 |
| 18.5945 | 2176.04 | 84.89 |
| 18.8776 | 299.07 | 10.21 |
| 19.1734 | 700.17 | 27.32 |
| 19.5663 | 532.16 | 15.57 |
| 19.8082 | 455.57 | 8.89 |
| 19.9242 | 604.64 | 20.64 |
| 20.3383 | 217.72 | 5.31 |
| 20.926 | 132.91 | 4.54 |
| 21.3168 | 268.3 | 6.54 |
| 21.5201 | 1173.39 | 40.06 |
| 22.2186 | 1727.07 | 50.53 |
| 22.3795 | 1044.9 | 30.57 |
| 22.7643 | 243.85 | 8.32 |
| 23.4632 | 316.04 | 10.79 |
| 23.6243 | 256.97 | 7.52 |
| 23.8429 | 216.5 | 7.39 |
| 24.4267 | 409.84 | 17.99 |
| 24.8313 | 216.33 | 6.33 |
| 25.1209 | 394.43 | 11.54 |
| 25.5696 | 246.79 | 4.81 |
| 25.8873 | 1114.42 | 54.35 |
| 26.1424 | 209.25 | 5.1 |
| 26.8214 | 333.35 | 13 |
| 27.0146 | 263.65 | 5.14 |
| 27.4092 | 69.24 | 3.38 |
| 27.8546 | 97.48 | 3.8 |
| 28.3165 | 64.86 | 2.53 |
| 29.3219 | 286.3 | 9.77 |
| 29.5527 | 258.1 | 5.03 |
| 30.042 | 76.46 | 2.24 |
| 31.3761 | 120.75 | 4.71 |
| 32.0435 | 92.78 | 3.62 |
| 32.6288 | 262.21 | 12.79 |
| 32.8809 | 129.81 | 3.8 |
| 33.6089 | 53.43 | 3.13 |
| 34.1518 | 81.06 | 3.95 |
| 34.612 | 127.75 | 7.48 |
| 34.8988 | 68 | 3.98 |
| 35.4786 | 25.71 | 8.03 |
| 35.9233 | 191.73 | 9.35 |
| 37.738 | 79.27 | 6.18 |
| 38.2855 | 126.18 | 7.38 |

TABLE 2

XRPD Peak Table for Formula IVa, Form II

| Pos. [°2Th.] | Height [cts] | Rel. Int. [%] |
|---|---|---|
| 3.9984 | 117.09 | 2.37 |
| 8.0138 | 1336.72 | 18 |
| 11.3827 | 224.6 | 4.54 |
| 12.0385 | 87.72 | 1.77 |
| 12.6947 | 184.18 | 4.34 |
| 12.8444 | 152.64 | 2.57 |
| 13.3055 | 65 | 1.31 |
| 13.9013 | 523.85 | 8.82 |
| 14.0548 | 797.67 | 13.43 |
| 15.0294 | 962.8 | 19.45 |
| 15.9544 | 1791.97 | 36.2 |
| 16.1082 | 1408.2 | 23.71 |
| 16.2247 | 818.1 | 11.02 |
| 17.0556 | 2219.26 | 52.31 |
| 17.4609 | 420.73 | 9.51 |
| 17.5046 | 210.36 | 4.76 |
| 17.5563 | 876.5 | 14.76 |
| 17.9007 | 236.58 | 4.78 |
| 18.3249 | 1603.96 | 37.8 |
| 18.4775 | 558.45 | 7.52 |
| 19.0115 | 1163.48 | 27.42 |
| 19.2203 | 302.37 | 8.14 |
| 19.7367 | 709.19 | 19.1 |
| 20.1462 | 417.93 | 7.04 |
| 20.5553 | 2183.44 | 58.81 |
| 21.2475 | 846.44 | 17.1 |
| 21.4399 | 2001.53 | 60.65 |
| 21.824 | 68.34 | 1.38 |
| 22.2072 | 224.05 | 6.04 |
| 22.6132 | 490.01 | 6.6 |
| 22.9077 | 2474.93 | 100 |
| 23.328 | 909.07 | 30.27 |
| 23.4151 | 817.53 | 18.15 |
| 23.7176 | 693.66 | 26.95 |
| 23.9708 | 396.55 | 13.21 |
| 24.1394 | 753.76 | 25.1 |
| 24.7039 | 469.31 | 20.84 |
| 25.2844 | 235.01 | 6.52 |
| 25.6754 | 520.53 | 28.89 |
| 25.8972 | 140.74 | 4.69 |
| 26.3569 | 423.22 | 16.44 |
| 26.9483 | 107.26 | 4.76 |
| 27.4833 | 533.45 | 20.72 |
| 27.8235 | 225.34 | 10.01 |
| 28.0395 | 116.37 | 5.17 |
| 28.4281 | 79.4 | 8.81 |
| 28.972 | 39.15 | 3.48 |
| 29.3137 | 78.33 | 3.48 |
| 29.76 | 173.83 | 7.72 |
| 30.0643 | 168.75 | 9.37 |
| 30.3742 | 129.63 | 7.19 |
| 31.2476 | 94.42 | 5.24 |
| 31.5068 | 95.48 | 3.18 |
| 31.8006 | 96.82 | 6.45 |
| 32.6093 | 156.74 | 6.96 |
| 33.1359 | 106.65 | 5.92 |
| 33.4314 | 79.07 | 2.63 |
| 33.7371 | 103 | 4.57 |
| 34.1029 | 83.38 | 4.63 |
| 34.5281 | 113.17 | 6.28 |
| 35.5035 | 155.06 | 12.05 |
| 37.0913 | 70.23 | 4.68 |
| 37.4596 | 71.86 | 5.58 |
| 38.0724 | 38.45 | 2.56 |
| 38.6032 | 97.15 | 6.47 |
| 39.4142 | 99.04 | 5.5 |

Example 3. Preparation of Ethyl 3-oxo-3-(1r,4r)-4-phenylcyclohexyl)-2-(3-(trifluoromethyl)benzyl)propanoate (Formula IIIa)

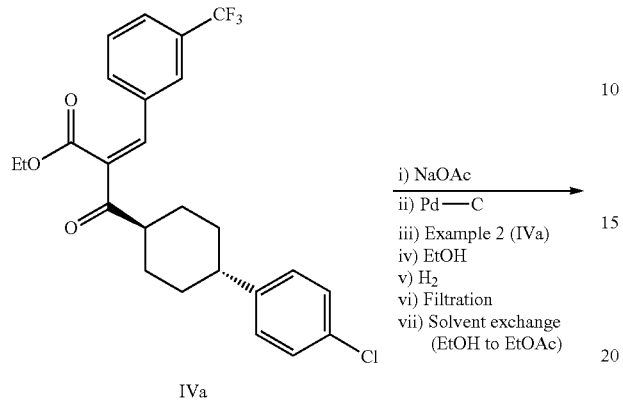

The compound of Formula IIIa can be prepared by a variety of methods, such as described for Compound 11 in U.S. Pat. No. 8,685,973.

Alternatively, the compound of Formula IIIa can be prepared according to the following method.

1. Charge anhydrous sodium acetate (52.9 g, 1.2 eq) to the hydrogenator.
2. Charge 5% Pd—C catalyst, Type 394, 50% wet paste (4.375 g, 1.75 wt %) to the vessel
3. Charge product of Example 2 (250 g, 0.538 mol, 1.00 eq) to the vessel. Then inert the vessel with nitrogen.
4. Charge ethanol (1250 mL, 5 vol) to the vessel, then re-inert the vessel, and commence stirring at 200 rpm.
5. Pressurise & purge the vessel with hydrogen, then apply 3 barg (4 barA) hydrogen pressure to the headspace. Increase the stirrer speed to achieve good gas-liquid mixing in the vessel and maintain the batch at 20-30° C.
6. Allow the hydrogenation to proceed until no further hydrogen uptake is apparent.
7. Continue the hydrogenation for at least one hour past the point of apparent zero uptake, then sample the batch for analysis. During the hold period for the IPC result, restore the hydrogen atmosphere (3 barg/4 barA), and raise the batch to about 30° C.
8. Filter the reaction mixture through a Hyflo Supercel pad (37.5 g, 0.15 wt) maintaining a nitrogen blanket throughout.
9. Charge ethanol (250 mL, 1 vol) to the reactor, agitate for 5-10 minutes at 20 to 25° C. and use as a filter wash.
10. Charge ethanol (125 mL, 0.5 vol) to the reactor, agitate for 5-10 minutes at 20 to 25° C. and use as a filter wash.
11. Give a final wash to the filter cake with Ethanol (125 mL, 0.5 vol).
12. Transfer the filtrate and washes back to the hydrogenation vessel without intermediate cleaning, and distil the contents of the reactor to approximately 1.5 volumes at ≤45° C. under vacuum.
13. Charge ethyl acetate (750 mL, 3 vols) to the vessel
14. Charge deionised water (250 mL, 1 vol) to the vessel
15. Charge 10% w/w aq Sodium Carbonate solution (0.52 eq, 270 mL of solution).
16. Stir and adjust to 15-25° C., then hold for 30-45 mins
17. Polish-filter the batch to a clean vessel
18. Charge ethyl acetate (250 mL, 1 vol) to the first vessel and transfer through the filter and lines as a wash
19. Stir the batch at 15-25° C., then after about 10 mins, sample the batch and check that the pH is >7 (papers). If not, add further sodium carbonate (solid or solution) to achieve this. Make a second pH check at least 10 mins (with stirring) after the first, to ensure that the pH is stable at >7.
20. Settle the batch for at least 15 mins, then separate the lower aqueous phase.
21. Charge deionised water (375 mL, 1.5 vol) to the vessel and stir at 15-25° C. for at least 10 minutes.
22. Settle the batch for at least 30 mins, then separate the lower aqueous phase.
23. Charge ethanol (150 mL, 0.6 vol) to the batch.
24. Distil from the vessel under vacuum, aiming for a vessel temperature around 35-40° C. (corresponds to a vacuum of ca 250 mbar). Reduce the batch volume down to about 2 vols.
25. Charge ethyl acetate (750 mL, 3 vols) to the vessel (brings batch to approximately 5 vols total), then distil back down to about 2 vols, under vacuum.
26. Charge ethyl acetate (750 mL, 3 vols) to the vessel (batch vol total now approximately 5 vols), then distil back down to 3 volumes, under vacuum.
27. Charge ethyl acetate (500 mL, 2 vols) to the vessel, then distil back down a reactor level of 3 volumes, at atmospheric pressure.
28. Charge ethyl acetate (500 mL, 2 vols) to the vessel, then distil back down a reactor level of 3 volumes at atmospheric pressure.

The characterization data of the title compound were the same as described for Compound 11 in U.S. Pat. No. 8,685,973.

Example 4. Preparation of 2-amino-64(1r,4r)-4-phenylcyclohexyl)-5-(3-(trifluoromethyl)benzyl)pyrimidin-4(3H)-one Monohydrate (Formula II)

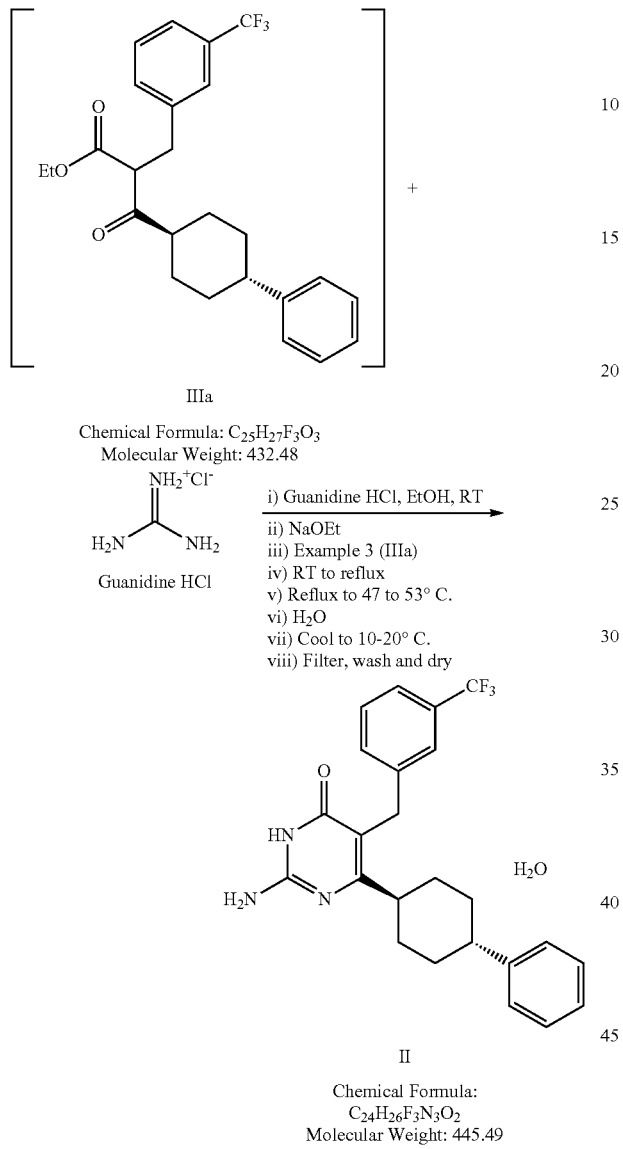

The method of preparing the compound of Formula II proceeded as follows:

1. Charge guanidine hydrochloride (39.1 g, 5 eq) to vessel at ambient temperature.
2. Charge ethanol (0.36 vol, 12.9 mL) direct to the vessel, but do not commence stirring.
3. Charge 21% w/w sodium ethoxide solution (119.4 g, 4.5 eq). Commence stirring at 15-25° C.
4. Charge ethanol (0.56 vol, 20 mL) as a rinse.
5. Repeat the rinse with ethanol (0.56 vol, 20 mL).
6. Agitate for about 30 minutes at 20 to 25° C. and confirm that a free flowing, lump-free slurry is present. If not, stir for an additional 30 mins.
7. Charge the ethyl acetate solution of Example 3 through dry lines (88.5 g soln at 40% w/w=35.4 g the product of Example 3, 1.00 eq) at 20 to 30° C.
8. Rinse in the charge with ethyl acetate (19.0 g, ca 21.2 mL, 2.64 eq)
9. Heat the reaction mixture to reflux and maintain at reflux (approx. 75 to 78° C. is expected) for 4 to 5 hours.
10. Adjust the batch temperature to 47 to 53° C., and meanwhile prepare 50% w/w aqueous acetic acid (39.3 g, 4 eq), then add to the batch over at least 5-10 mins. The addition is very mildly exothermic. Hold the batch at 47 to 53° C. throughout the following steps 11 to 17.
11. Perform a slow addition of water (40 mL, 1.13 vol) over at least 15-20 mins
12. Seed the batch with title compound seed (18 mg, 0.05% w/w), pre-slurried in a mixture of ethanol (0.09 mL, 0.0025 vol) and purified water (0.09 mL, 0.0025 vol)
13. Perform a slow addition of water (40 mL, 1.13 vol) over at least 15-20 mins
14. Seed the batch with title compound seed (18 mg, 0.05% w/w), pre-slurried in a mixture of ethanol (0.09 mL, 0.0025 vol) and purified water (0.09 mL, 0.0025 vol)
15. Perform a slow addition of water (40 mL, 1.13 vol) over at least 15-20 mins
16. Perform a slow addition of water (40 mL, 1.13 vol) over about at least 15-20 mins
17. Cool the batch to 10-20° C. (target 15° C.) over about 1-2 hours, and hold for at least two hours.
18. Meanwhile, prepare a mixture of EtOH, EtOAc and water (approx 5 vols) using the ratios specified. Measure each component separately, then mix.
19. Filter the batch at 15° C. to recover the product
20. Charge a portion of the mixture prepared in step 19 above (70 mL, 2 vols) to the vessel as a rinse, cool to 10-20° C. (target: 15° C.), then transfer to the filter as a wash, and allow to soak into the cake before applying vacuum.
21. Charge a second portion of the mixture prepared at step 19 above (70 mL, 2 vols) to the vessel as a rinse, cool to 10-20° C. (target: 15° C.), then transfer to the filter as a wash, and allow to soak into the cake before applying vacuum.
22. Deliquor the batch thoroughly
23. Dry the crude title compound under vacuum at approximately 45±3° C. (42-48° C.) for at least 6 hours with a nitrogen bleed.
24. Once the solid is determined to be dry enough to be physically broken up, increase the drying temperature to 60±3° C. (57-63° C.). The resulting solid is maintained at that temperature until the set limit for loss on drying is met.

$^1$H-NMR (500 MHz; DMSO-d$_6$): δ 10.79 (s, 1H), 7.58 (s, 1H), 7.53-7.47 (m, 3H), 7.27 (t, 2H), 7.22 (d, 2H), 7.16 (t, 1H), 6.33 (s, 1H), 3.83 (s, 2H), 2.78-2.73 (m, 1H), 2.46-2.41 (m, 1H), 1.78-1.65 (m, 4H), 1.51-1.39 (m, 4H). Melting Point (DSC): initial broad melting with a maximum peak endotherm at 196.3° C. with concomitant loss of water based on thermogravimetric analysis (TGA), followed by a sharp melt at 275.1° C.

TABLE 3

XRPD Peak Table for Formula II

| Pos. [°2Th.] | Height [cts] | Rel. Int. [%] |
|---|---|---|
| 5.0683 | 397.37 | 1.29 |
| 10.7166 | 1951.22 | 6.33 |
| 11.1182 | 2675.61 | 8.68 |

TABLE 3-continued

XRPD Peak Table for Formula II

| Pos. [°2Th.] | Height [cts] | Rel. Int. [%] |
| --- | --- | --- |
| 11.7602 | 10237.89 | 39.87 |
| 12.5702 | 4729.26 | 15.35 |
| 13.0145 | 3686.05 | 14.35 |
| 13.5885 | 280.87 | 1.09 |
| 13.7824 | 1173.62 | 4.57 |
| 15.3212 | 5027.75 | 16.32 |
| 15.9068 | 2704.32 | 12.29 |
| 17.9479 | 8100.08 | 36.8 |
| 18.3215 | 3900.85 | 17.72 |
| 18.9944 | 497.36 | 1.94 |
| 19.715 | 8943.27 | 40.63 |
| 20.0642 | 19259.96 | 100 |
| 20.3767 | 405.27 | 1.58 |
| 21.3307 | 4697.67 | 39.64 |
| 21.6446 | 5668.46 | 51.5 |
| 22.1969 | 955.85 | 4.34 |
| 22.3607 | 1502.55 | 7.8 |
| 22.8788 | 405.49 | 1.58 |
| 23.141 | 4867.36 | 34.75 |
| 23.6505 | 195.46 | 1.01 |
| 24.0476 | 593.77 | 3.08 |
| 24.4292 | 2226.76 | 10.12 |
| 25.317 | 1305.73 | 9.32 |
| 25.5929 | 315.49 | 1.64 |
| 26.1698 | 1230.22 | 5.59 |
| 26.374 | 2977.41 | 19.32 |
| 27.2512 | 156.13 | 1.62 |
| 28.0825 | 767.58 | 3.28 |
| 28.1506 | 1065.16 | 2.07 |
| 28.3155 | 672.86 | 2.62 |
| 28.6152 | 1065.35 | 6.91 |
| 28.8215 | 701.29 | 4.55 |
| 29.9381 | 341.61 | 1.55 |
| 30.1848 | 163.96 | 0.64 |
| 30.4375 | 455.91 | 2.37 |
| 31.0447 | 770.7 | 5.5 |
| 31.5592 | 106.29 | 1.38 |
| 32.1275 | 245.38 | 1.27 |
| 32.498 | 1016.71 | 2.64 |
| 32.6762 | 832.79 | 4.32 |
| 33.747 | 124.11 | 0.64 |
| 34.5345 | 437.26 | 6.24 |
| 34.9531 | 948.64 | 8.62 |
| 36.0611 | 191.77 | 1.99 |
| 36.5592 | 348.26 | 3.16 |
| 37.4131 | 114.17 | 0.89 |
| 37.8266 | 155.69 | 1.21 |
| 38.2118 | 233.34 | 1.82 |
| 38.6715 | 225.34 | 2.34 |
| 39.2572 | 150.31 | 1.17 |
| 39.7222 | 620.35 | 2.42 |

Example 5. Preparation of 64(1r,4r)-4-phenylcyclohexyl)-5-(3-(trifluoromethyl)benzyl)pyrimidine-2,4 (1H,3H)-dione (Formula I)

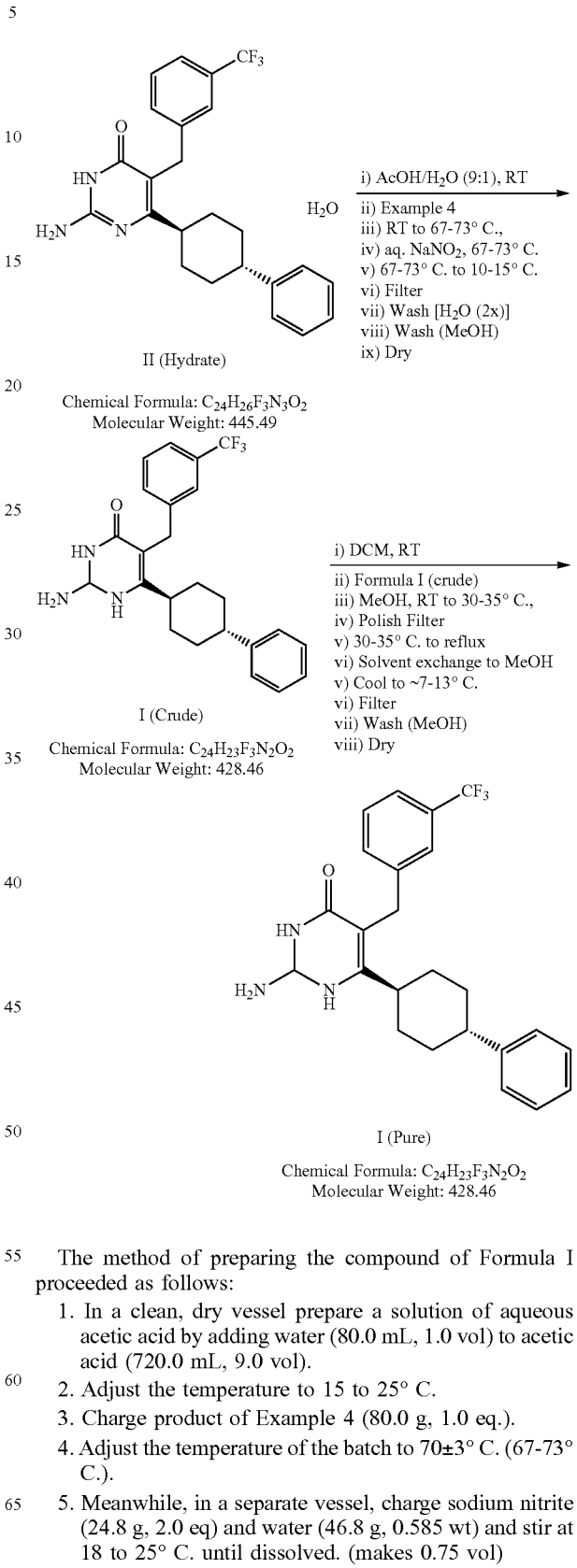

The method of preparing the compound of Formula I proceeded as follows:
1. In a clean, dry vessel prepare a solution of aqueous acetic acid by adding water (80.0 mL, 1.0 vol) to acetic acid (720.0 mL, 9.0 vol).
2. Adjust the temperature to 15 to 25° C.
3. Charge product of Example 4 (80.0 g, 1.0 eq.).
4. Adjust the temperature of the batch to 70±3° C. (67-73° C.).
5. Meanwhile, in a separate vessel, charge sodium nitrite (24.8 g, 2.0 eq) and water (46.8 g, 0.585 wt) and stir at 18 to 25° C. until dissolved. (makes 0.75 vol)

6. The sodium nitrite solution from Step 5 (total ~71.6 g, 0.898 wt) is to be added in portions (see steps below) at a steady rate such that the period of active addition is at least 3 hours, whilst maintaining the reaction temperature at 67-73° C. Stop the addition if necessary to maintain temperature control, and then resume at the same rate. Stop the addition to perform seeding during the addition, as defined below.
7. Add 40% of the sodium nitrite charge (28.6 g, 23 mL) over a minimum of 70 minutes.
8. Seed the batch with a slurry of title compound seeds (40 mg, 0.0005 wt) in 85% v/v acetic acid in water (0.025 vol, 2 mL), hold for 8-10 mins, check for crystallisation, then proceed.
9. Add 5% of the sodium nitrite solution (3.6 g, ~2.9 mL) over at least 10 mins.
10. Repeat the seeding operation with a slurry of title compound seeds (40 mg, 0.0005 wt) in 85% v/v acetic acid in water (0.025 vol, 2 mL). Hold for 8-10 mins, check for crystallisation, then proceed.
11. Add 5% of the sodium nitrite solution (3.6 g, ~2.9 mL) over at least 10 mins.
12. Repeat the seeding operation with a slurry of title compound seeds (40 mg, 0.0005 wt) in 85% v/v acetic acid in water (0.025 vol, 2 mL). Hold for 8-10 mins, check for crystallisation, then proceed.
13. Add the remaining 50% of the sodium nitrite solution over at least 90 mins.
14. Rinse through any residual sodium nitrite solution with water (4.0 mL, 0.05 vol).
15. Hold the reaction mixture at 67 to 73° C. for 45 to 75 minutes and then sample for reaction completion.
16. Following reaction completion, cool the reaction mixture to 10-15° C. over a minimum of 2 hours, then hold for at least one hour.
17. Filter the batch, smoothing the cake as necessary, and compacting so as to achieve effective deliquoring.
18. Apply a chilled wash (10-15° C.) of 85% v/v acetic acid in water (160 mL, 2 vols) via the vessel. Allow to soak into the cake before applying vacuum
19. Apply a second chilled wash (10-15° C.) of 85% v/v acetic acid in water (160 mL, 2 vols) via the vessel. Allow to soak into the cake before applying vacuum. Deliquor the cake thoroughly.
20. Apply a final wash of chilled methanol (10-15° C.; 160 mL, 2 vols). Allow to soak into the cake before applying vacuum. Deliquor the cake thoroughly.
21. Dry the crude title compound under vacuum and a nitrogen bleed at 45±3° C. (42-48° C.) for at least 6 hours.
22. Once the solid is determined to be dry enough to be physically broken up, increase the drying temperature to 60±3° C. (57-63° C.). The resulting solid is maintained at that temperature until the set limit for loss on drying is met.

The crystallization of the compound of Formula I proceeded as follows:

1. Charge dichloromethane (420 mL, 8.4 vols wrt of crude title compound)
2. Charge the dried crude title compound (50.0 g, 1 eq) (assayed content not gross weight)
3. Charge methanol (85 mL, 1.7 vol) and warm the batch to about 30-35° C. to obtain a solution.
4. Polish-filter the batch to a clean vessel
5. Wash the source vessel, filter, and lines with a mixture of dichloromethane (130 mL, 2.6 vols) and methanol (25 mL, 0.50 vols), through to the crystalliser
6. Heat the batch to boiling at atmospheric pressure (38-40° C. expected), and commence the distillation of solvent, to remove a total of 20 vols. Initially, this will be mainly dichloromethane. During the distillation, add 1 vol of MeOH for each 1 vol of distillate collected, so as to keep the batch volume at roughly 13-14 volumes. Across the course of the solvent exchange the batch temperature will rise to about 65° C., and the jacket temperature can be raised as appropriate to maintain a reasonable distillation rate. During the distillation, perform the following seeding steps:
7. At about "3 vols" of solvent exchanged, seed the batch by pumping into the reactor a slurry of title compound seed (25 mg, 0.05 wt %) in methanol (1.25 mL, 0.025 vols). Perform this seeding whether or not the batch already appears to be crystallising, hold for about 10 mins, then note any changes in appearance of the batch.
8. At about "4 vols" of solvent exchanged, seed the batch by pumping into the reactor a slurry of title compound seed (25 mg, 0.05 wt %) in methanol (1.25 mL, 0.025 vols). Perform this seeding whether or not the batch already appears to be crystallising, hold for about 10 mins, then note any changes in appearance of the batch.
9. At about "5 vols" of solvent exchanged, seed the batch by pumping into the reactor a slurry of title compound seed (25 mg, 0.05 wt %) in methanol (1.25 mL, 0.025 vols). Hold for about 10 mins, and note whether the crystallisation has started. This step may be omitted if the batch is already substantially crystallising.
10. Once the batch temperature has become effectively constant, distil out a further "4 vols" of solvent (approx), to reduce the batch volume to about 10 vols.
11. Commence steady cooling of the batch to bring it from approximately 65° C. to 10±3° C. (7-13° C.; target: 10° C.) over at least two hours, then hold the batch in this range for at least two hours.
12. Filter the batch. Smooth and compress the cake as necessary to ensure effective deliquoring, but do not allow the cake to dry on the filter.
13. Charge methanol (100 mL, 2 vols) to the vessel, stir, and cool to 10-15° C.
14. Discharge the wash to the filter, allow to soak into the cake and then deliquor.
15. Charge methanol (100 mL, 2 vols) to the vessel, stir, and cool to 10-15° C.
16. Discharge the wash to the filter, allow to soak into the cake and then deliquor thoroughly.
17. Dry the pure solid corresponding to Formula I under vacuum at up to approximately 60° C. (batch temperature) for at least 8 hours using a nitrogen bleed.

The characterization data of the title product matched those of Example 6 of U.S. Pat. No. 8,685,973.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of preparing a compound of Formula I:

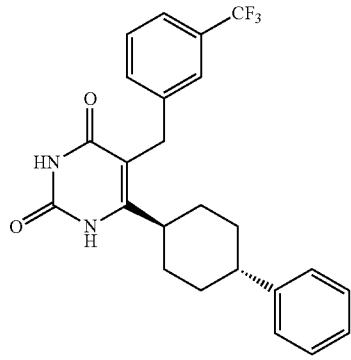

the method comprising:
(a) forming a first reaction mixture comprising an oxidizing agent and a compound of Formula II, or a hydrate thereof:

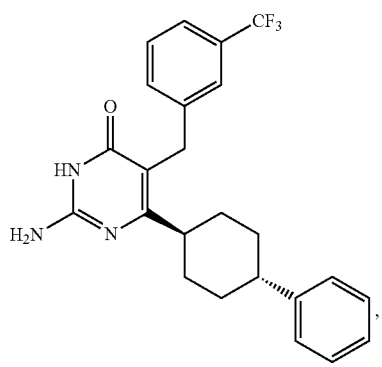

wherein the oxidizing agent comprises at least one of sodium nitrite (NaNO$_2$), potassium nitrite (KNO$_2$), tetrabutylammonium nitrite [(n-C$_4$H$_9$)$_4$ N$^+$NO$_2$$^-$], nitrosylsulfuric acid, [HOSO$_2$—O—N=O], methyl nitrite (CH$_3$O—N=O), ethyl nitrite (CH$_3$CH$_2$O—N=O), n-propylnitrite (CH$_3$CH$_2$CH$_2$O—N=O), isopropyl nitrite [(CH$_3$)$_2$CHO—N=O], n-butyl nitrite [CH$_3$(CH$_2$)$_3$O—N=O], isobutyl nitrite [(CH$_3$)$_2$CH(CH$_2$)$_2$O—N=O], isopentyl nitrite [(CH$_3$)$_2$CH(CH$_2$)$_2$O—N=O], or phenyl nitrite (C$_6$H$_5$O—N=O),
to prepare the compound of Formula I.

2. The method of claim 1, wherein the first reaction mixture further comprises a first acid comprising hydrochloric acid, sulfuric acid, formic acid, acetic acid, propanoic acid, butyric acid, hexanoic acid, octanoic acid, trifluoroacetic acid, tetrafluoroboric acid (HBF$_4$), or mixtures thereof.

3. The method of claim 1, wherein the first reaction mixture further comprises a first solvent comprising N,N-dimethylformamide (DMF), N,N-dimethylacetamide (DMAc), isopropanol, 2-methyltetrahydrofuran (2-MeTHF), tetrahydrofuran, water, or mixtures thereof.

4. The method of claim 1, wherein the compound of Formula II is the monohydrate form:

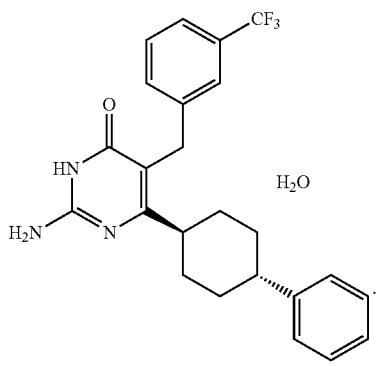

5. The method of claim 1, wherein the first reaction mixture comprises acetic acid, sodium nitrite and the monohydrate form of the compound of Formula II.

6. The method of claim 1, further comprising:
(a1) dissolving the compound of Formula I in a solvent mixture comprising methanol in an amount of about 15% (v/v) and dichloromethane in an amount of about 85% (v/v);
(a2) heating the solvent mixture to remove dichloromethane and adding methanol to the solvent mixture to replace the removed dichloromethane, thereby preparing a methanol solvent mixture; and
(a3) cooling the methanol solvent mixture, thereby forming crystalline Formula I.

7. The method of claim 1, wherein the compound of Formula II, or the hydrate thereof, is prepared by the method comprising:
(b) forming a second reaction mixture comprising guanidine and salts thereof, and a compound of Formula III:

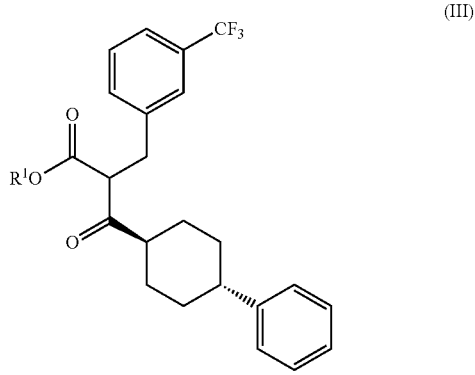

to prepare the compound of Formula II, or the hydrate thereof,
wherein R$^1$ is C$_{1-6}$ alkyl.

8. The method of claim 7, wherein the compound of Formula III is the compound of Formula IIIa:

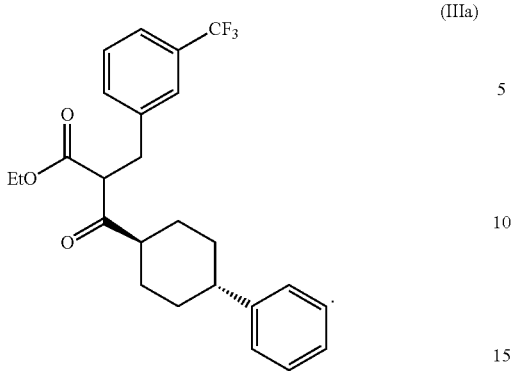

(IIIa)

9. The method of claim 7, wherein the second reaction mixture further comprises a second solvent comprising ethanol, isopropanol, methyl acetate, ethyl acetate, isopropyl acetate, N,N-dimethylformamide (DMF), N,N-dimethylacetamide (DMAc), 2-methyltetrahydrofuran (2-MeTHF), tetrahydrofuran (THF), water, or mixtures thereof.

10. The method of claim 7, wherein the second reaction mixture comprises ethyl acetate, guanidine free base, and the compound of Formula IIIa, to prepare the monohydrate form of the compound of Formula II:

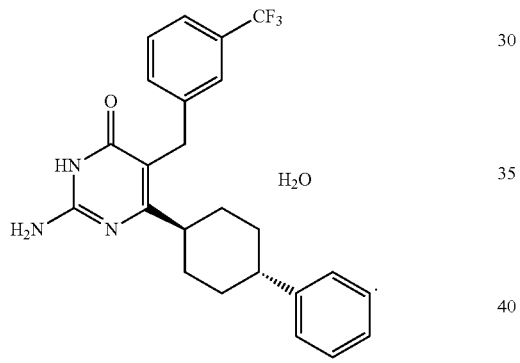

11. The method of claim 7, wherein prior to step (b), the method further comprises:
   (b1) forming a third reaction mixture comprising guanidine salt and a base to prepare the guanidine free base.

12. The method of claim 11, wherein the third reaction mixture further comprises a third solvent comprising methanol, ethanol, n-propanol, iso-propanol, water, or mixtures thereof.

13. The method of claim 12, wherein the third reaction mixture further comprises a water scavenger.

14. The method of claim 11, wherein prior to step (b), the method further comprises:
   (b1) forming the third reaction comprising ethanol, guanidine hydrochloride salt and sodium ethoxide to prepare the guanidine free base.

15. The method of claim 11, wherein following step (b), the method further comprises:
   (b2) adding water to the second reaction thereby crystallizing the compound of Formula II, or the hydrate thereof.

16. The method of claim 7, wherein the compound of Formula III is prepared by:
   (c) forming a fourth reaction mixture comprising a reducing agent and a compound of Formula IV:

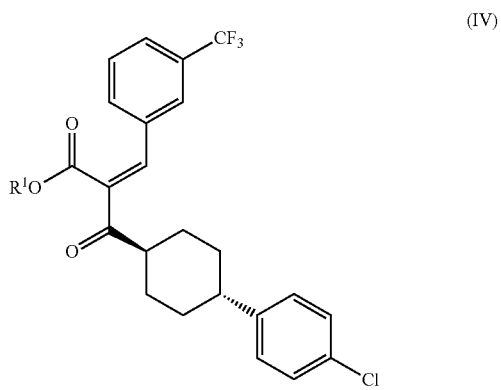

(IV)

wherein the reducing agent is the hydrogenation catalyst comprising palladium on carbon (Pd—C), palladium on silicon dioxide, palladium on calcium carbonate, platinum on carbon, palladium hydroxide, platinum hydroxide, palladium(II) chloride, Raney Nickel, rhodium on alumina, rhodium(III) chloride trihydrate/Aliquat 336 (N-methyl N-trioctylammonium chloride), Ru(BINAP)]$_2$*NEt$_3$, or nickel boride (Ni$_2$B),
to prepare the compound of Formula III.

17. The method of claim 16, wherein the fourth reaction mixture comprises a fourth solvent comprising methanol, ethanol, n-propanol, iso-propanol, n-butanol, ethyl acetate, isopropyl acetate, n-butyl acetate, formic acid, acetic acid, trifluoroacetic acid, water, or mixtures thereof.

18. The method of claim 16, wherein the compound of Formula IV is the compound of Formula IVa:

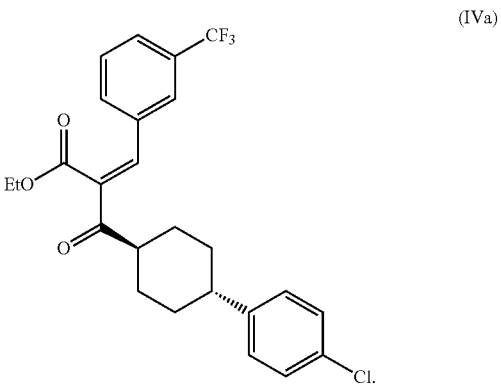

(IVa)

19. The method of claim 16, wherein the fourth reaction mixture comprises ethanol, 5% Pd—C, hydrogen, sodium acetate, and the compound of Formula IV is the compound of Formula IVa:

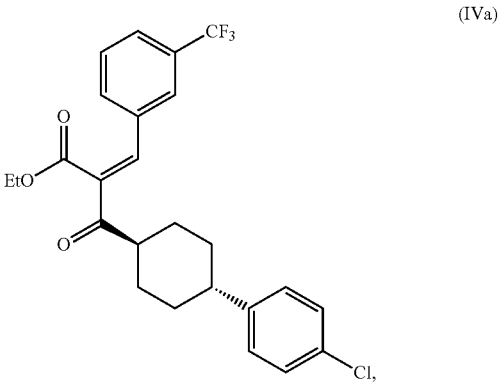 [SMILES: CCOC(=O)/C(=C\c1cccc(C(F)(F)F)c1)C(=O)[C@H]1CC[C@H](c2ccc(Cl)cc2)CC1]

(IVa)

thereby preparing the compound of Formula IIIa:

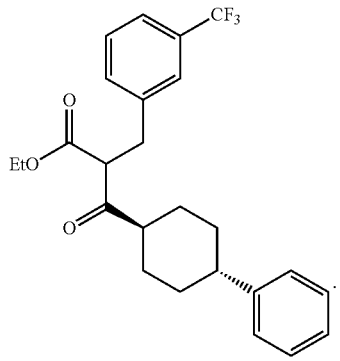

(IIIa)

20. The method of claim 16, wherein the compound of Formula IV is prepared by:
  (d) forming a fifth reaction mixture comprising a first amine base, a second acid, 3-trifluoromethylbenzaldehyde, and a compound of Formula V:

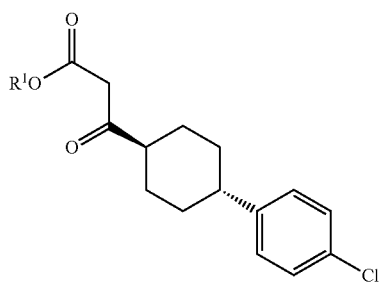

(V)

to prepare the compound of Formula IV.

21. The method of claim 20, wherein the first amine base comprises triethylamine, N,N-diisopropyl ethylamine (DIPEA), N,N-dimethyl isopropylamine (DIMPA), piperidine, 1-ethylpiperidine, N-methylmorpholine, N-methylpyrrolidine, N,N-dimethylamine, piperazine, N-methylpiperazine, tris(Hydroxymethyl)methylamine [(HOCH$_2$)$_3$CNH$_2$], benzylamine, pyridine, N,N-dimethylaniline, N,N-diethylaniline, 2,6-lutidine, 2,4,6-collidine, 4-dimethyl aminopyridine (DMAP), quinuclidine, 4-pyrrolidinopyridine, 1,4-diazabicyclo[2.2.2]octane (DABCO), or mixtures thereof.

22. The method of claim 20, wherein the compound of Formula V is the compound of Formula Va:

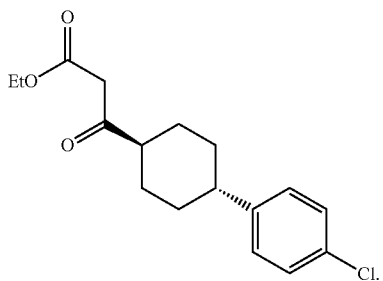

(Va)

23. The method of claim 20, wherein the fifth reaction mixture further comprises a fifth solvent comprising methanol, ethanol, n-propanol, iso-propanol, acetonitrile, dichloromethane, diethyl ether, 2-methyltetrahydrofuran (2-MeTHF), cyclopropylmethyl ether (CPME), tetrahydrofuran, 2,2,2-trifluoroethanol, toluene, xylene, mesitylene, or mixtures thereof.

24. The method of claim 20, wherein the fifth reaction mixture comprises ethanol, piperidine, acetic acid, 3-trifluoromethylbenzaldehyde, and the compound of Formula V is the compound of Formula Va:

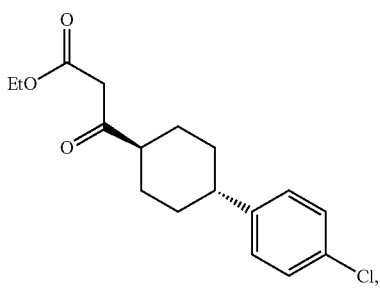

(Va)

thereby preparing the compound of Formula IVa:

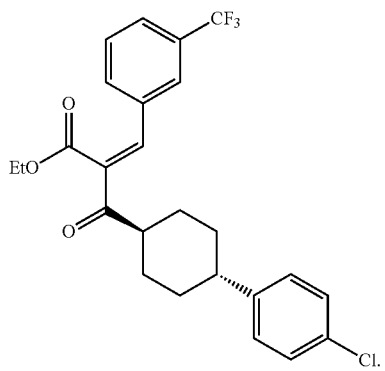

(IVa)

25. The method of claim 20, further comprising:
  (d1) adding to the fifth reaction mixture a crystalline seed of the compound of Formula IV to prepare the crystalline form of the compound of Formula IV.

26. The method of claim 20, wherein the compound of Formula V is prepared by:
  (e1) forming a seventh reaction mixture comprising isopropylidene malonate, a carboxyl coupling agent, a second amine base, and a compound of Formula VI:

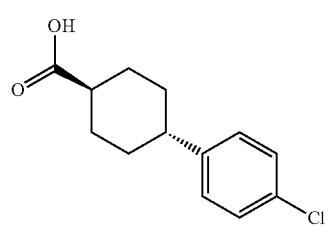

(VI)

to prepare an intermediate mixture; and
  (e2) heating a sixth reaction mixture comprising the intermediate mixture, thereby preparing the compound of Formula V.

27. The method of claim 26, wherein the carboxyl activating agent is dicyclohexylcarbodiimide (DCC), N,N'-diisopropylcarbodiimide (DIC), 1-ethyl-3-(3-dimethylaminopropyl)carbodiimide (EDC), 1-ethyl-3-(3-dimethylaminopropyl)carbodiimide HCl (EDAC), bis[[4-(2,2-dimethyl-1,3-dioxolyl)]methyl]carbodiimide (BDDC), N-cyclohexyl-N'-(2-morpholinoethyl)carbodiimide methyl-p-toluenesulfonate, 1-[3-(dimethylamino)propyl]-3-ethylcarbodiimide methiodide, thionyl chloride, oxalyl chloride, 2-ethoxy-1-ethoxycarbonyl-1,2-dihydroquinoline (EEDQ), carbonyl diimidazole, bis(1,2,4-triazolyl)methanone, n-propanephosphonic acid anhydride, ethylmethylphosphonic anhydride (EMPA), cyanuric chloride, 2-chloro-4,6-dimethoxy-1,3,5-triazine (CDMT), 4-(4,6-dimethoxy-1,3,5-triazin-2-yl)-4-methylmorphonium chloride (DMTMM), guanidinium salt, uronium salt, hexafluorophosphate benzotriazole tetramethyl uronium (HBTU), hexafluorophosphate azabenzotriazole tetramethyl uronium (HATU), 2-(1H-Benzotriazole-1-yl)-1,1,3,3-tetramethylaminium tetrafluoroborate (TBTU), O-(2-Oxo-1(2H)pyridyl)-N,N,N',N'-tetramethyluronium tetrafluoroborate (TPTU), or N-[[[(1-Cyano-2-ethoxy-2-oxoethylidene)amino]oxy](dimethylamino)methylene]-N-methyl-methanaminium tetrafluoroborate (TOTU).

28. The method of claim 26, wherein the second amine base comprises triethylamine, N,N-diisopropyl ethylamine (DIPEA), N,N-dimethyl isopropylamine (DIMPA), 1-ethylpiperidine, N-methylmorpholine, N-methylpyrrolidine, pyridine, N,N-dimethylaniline, N,N-diethylaniline, 2,6-lutidine, 2,4,6-collidine, 4-dimethyl aminopyridine (DMAP), quinuclidine, 4-pyrrolidinopyridine, 1,4-diazabicyclo[2.2.2]octane (DABCO), or mixtures thereof.

29. The method of claim 26, wherein the seventh reaction mixture further comprises a seventh solvent comprising acetonitrile, tetrahydrofuran, 2-methyltetrahydrofuran, N,N-dimethylformamide, N,N-dimethylacetamide, dichloromethane, chloroform, toluene, or mixtures thereof.

30. The method of claim 26, wherein the seventh reaction mixture comprises dichloromethane, isopropylidene malonate, EDAC, dimethylaminopyridine (DMAP), and the compound of Formula VI.

31. The method of claim 26, wherein the sixth reaction mixture further comprises a sixth solvent comprising methanol, ethanol, n-propanol, iso-propanol, n-butanol, t-butanol, pentanol, hexanol, or mixture thereof.

32. The method of claim 26, further comprising the step of
(e3) adding heptane to the sixth reaction mixture to crystallize the compound of Formula V.

33. A method of preparing a compound of Formula I:

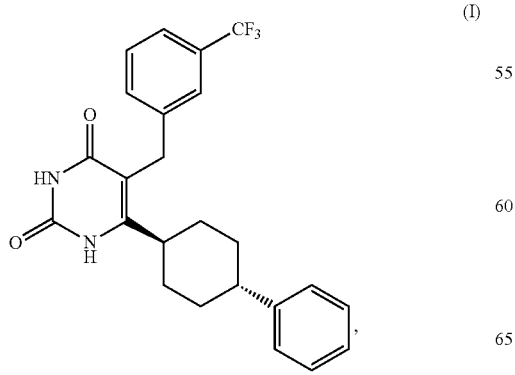

the method comprising:
(e1) forming a seventh reaction mixture comprising dichloromethane, isopropylidene malonate, 1-ethyl-3-(3-dimethylaminopropyl)carbodiimide HCl (EDAC), dimethylaminopyridine (DMAP), and a compound of Formula VI:

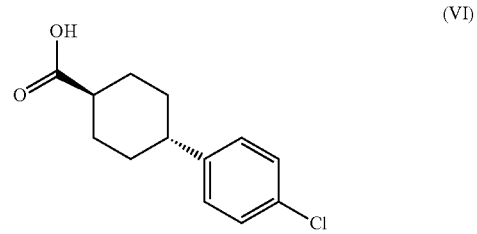 [SMILES: O=C(O)[C@H]1CC[C@H](c2ccc(Cl)cc2)CC1]

to prepare an intermediate mixture;
(e2) heating a sixth reaction mixture comprising the intermediate mixture and ethanol, thereby preparing a compound of Formula Va:

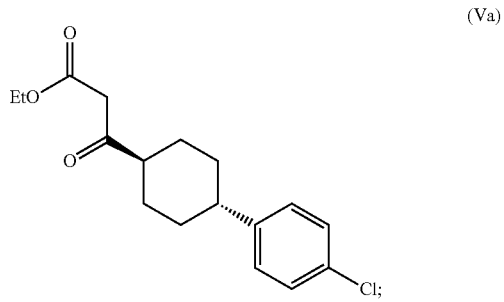 [SMILES: CCOC(=O)CC(=O)[C@H]1CC[C@H](c2ccc(Cl)cc2)CC1]

(e3) adding heptane to the sixth reaction mixture to crystallize the compound of Formula Va;
(d) forming a fifth reaction mixture comprising ethanol, piperidine, acetic acid, 3-trifluoromethylbenzaldehyde, and the compound of Formula Va, to prepare a compound of Formula IVa:

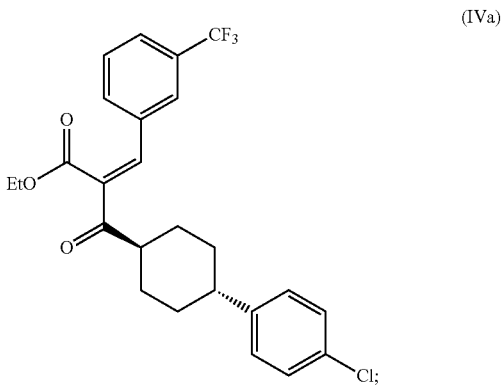 [SMILES: CCOC(=O)/C(=C\c1cccc(C(F)(F)F)c1)C(=O)[C@H]1CC[C@H](c2ccc(Cl)cc2)CC1]

(d1) adding to the fifth reaction mixture a crystalline seed of the compound of Formula IVa to prepare a crystalline form of the compound of Formula IVa;
(c) forming a fourth reaction mixture comprising ethanol, 5% Pd—C, hydrogen, sodium acetate, and the compound of Formula IVa, to prepare a compound of Formula IIIa:

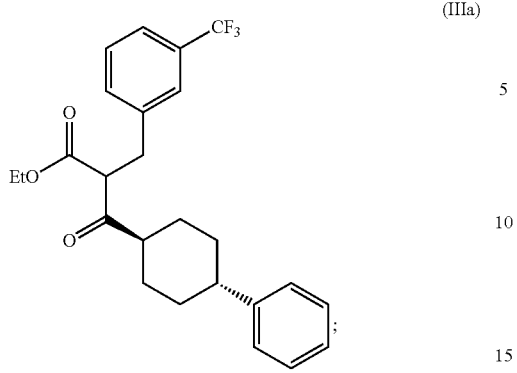

(IIIa)

(b1) forming a third reaction mixture comprising ethanol, guanidine hydrochloride salt and sodium ethoxide to prepare a guanidine free base;
(b) forming a second reaction mixture comprising ethyl acetate, the guanidine free base, and the compound of Formula IIIa, to prepare a monohydrate form of a compound of Formula II:

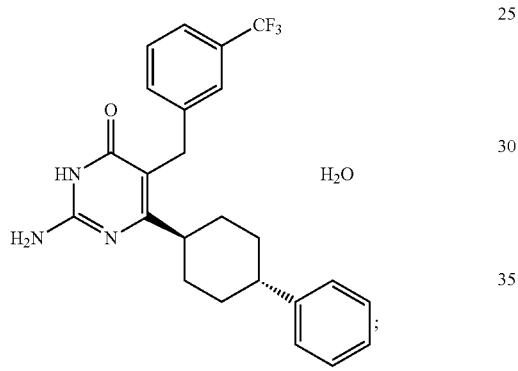

·H₂O and
(a) forming a first reaction mixture comprising acetic acid, sodium nitrite and the monohydrate form of the compound of Formula II, to prepare the compound of Formula I.

34. A method of preparing a compound of Formula II, or a hydrate thereof:

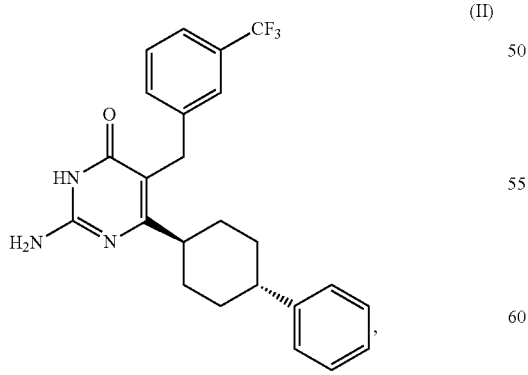

(II)

the method comprising:
(b) forming a second reaction mixture comprising guanidine and salts thereof, and a compound of Formula III:

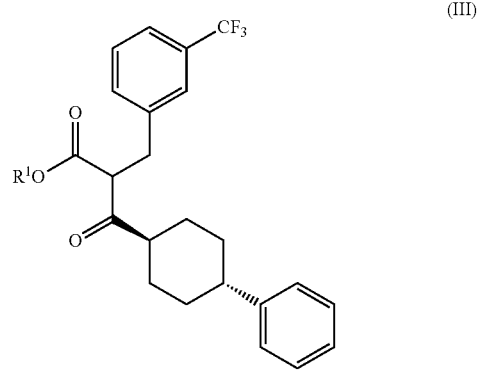

(III)

to prepare the compound of Formula II, or the hydrate thereof,
wherein R¹ is $C_{1-6}$ alkyl.

35. A compound of Formula II, or a hydrate thereof:

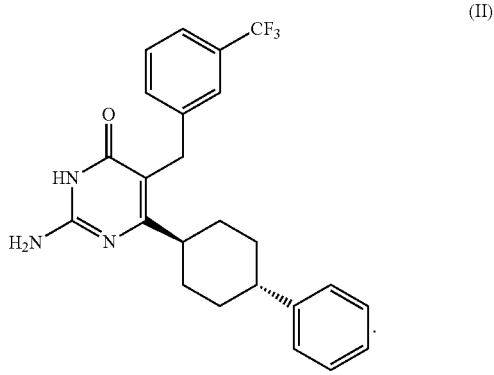 [SMILES: Nc1nc([C@H]2CC[C@H](c3ccccc3)CC2)c(Cc2cccc(C(F)(F)F)c2)c(=O)[nH]1]

(II)

36. A compound of Formula IVa:

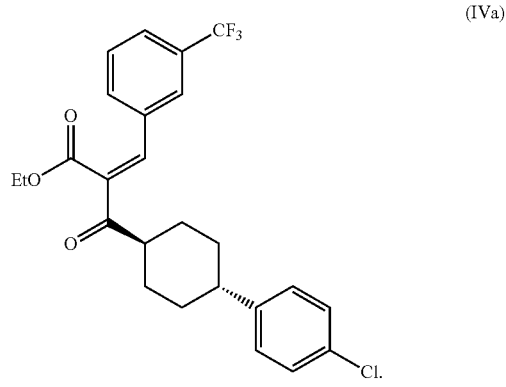 [SMILES: CCOC(=O)/C(=C\c1cccc(C(F)(F)F)c1)C(=O)[C@H]1CC[C@H](c2ccc(Cl)cc2)CC1]

(IVa)

37. A compound of Formula Va:

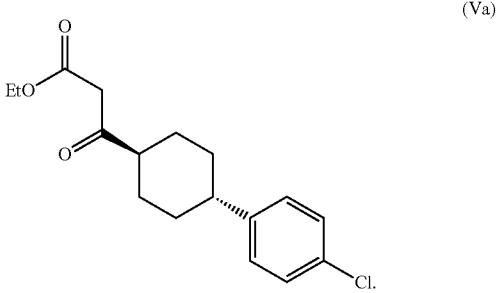 [SMILES: CCOC(=O)CC(=O)[C@H]1CC[C@H](c2ccc(Cl)cc2)CC1]

(Va)

* * * * *